United States Patent
Sanborn

(10) Patent No.: US 11,908,588 B2
(45) Date of Patent: Feb. 20, 2024

(54) SYSTEMS AND METHODS FOR GENETIC ANALYSIS OF METASTASES

(71) Applicant: Nantomics, LLC, Culver City, CA (US)

(72) Inventor: John Zachary Sanborn, Santa Cruz, CA (US)

(73) Assignee: NantOmics LLC, Culver City, CA (US)

( * ) Notice: Subject to any disclaimer, the term of this patent is extended or adjusted under 35 U.S.C. 154(b) by 883 days.

(21) Appl. No.: 15/755,096

(22) PCT Filed: Aug. 25, 2016

(86) PCT No.: PCT/US2016/048778
§ 371 (c)(1),
(2) Date: Feb. 26, 2018

(87) PCT Pub. No.: WO2017/035400
PCT Pub. Date: Mar. 2, 2017

(65) Prior Publication Data
US 2020/0227137 A1    Jul. 16, 2020

Related U.S. Application Data

(60) Provisional application No. 62/209,850, filed on Aug. 25, 2015.

(51) Int. Cl.
*G16H 70/60* (2018.01)
*G16H 50/50* (2018.01)
(Continued)

(52) U.S. Cl.
CPC ............... *G16H 70/60* (2018.01); *G16B 5/20* (2019.02); *G16B 10/00* (2019.02); *G16B 20/10* (2019.02);
(Continued)

(58) Field of Classification Search
CPC ........ G16B 20/20; G16B 10/00; G16B 40/00; G16B 5/20; G16B 20/10; G16B 45/00;
(Continued)

(56) References Cited

U.S. PATENT DOCUMENTS

| 6,545,139 B1 | 4/2003 | Thompson et al. |
| 7,917,306 B2 | 3/2011 | Frumkin et al. |

(Continued)

FOREIGN PATENT DOCUMENTS

| CN | 108475296 A | 8/2018 |
| JP | 2013-123420 | 6/2013 |

(Continued)

OTHER PUBLICATIONS

Michael L. Nickerson et al., Somatic alterations contributing to metastasis of a castration resistant prostate cancer, Sep. 2013, Hum Mutat, 34(9): 1231-1241 (Year: 2013).*

(Continued)

*Primary Examiner* — Robert A Sorey
*Assistant Examiner* — Kimberly A. Sass
(74) *Attorney, Agent, or Firm* — Martin Fessenmaier; Umberg Zipser LLP

(57) ABSTRACT

Contemplated systems and methods use identification and classification of somatic single nucleotide variants found in a primary tumor and metastases to determine phylogeny of the metastases.

15 Claims, 7 Drawing Sheets

(51) Int. Cl.
  *G16H 10/40* (2018.01)
  *G16H 50/20* (2018.01)
  *G16B 20/20* (2019.01)
  *G16B 10/00* (2019.01)
  *G16B 40/00* (2019.01)
  *G16B 5/20* (2019.01)
  *G16B 20/10* (2019.01)
  *G16B 20/40* (2019.01)

(52) U.S. Cl.
  CPC ............ *G16B 20/20* (2019.02); *G16B 20/40* (2019.02); *G16B 40/00* (2019.02); *G16H 10/40* (2018.01); *G16H 50/20* (2018.01); *G16H 50/50* (2018.01)

(58) Field of Classification Search
  CPC ........ G16B 20/00; G16H 70/60; G16H 50/50; G16H 10/40; G16H 50/20
  USPC .......................................................... 705/2
  See application file for complete search history.

(56) References Cited

U.S. PATENT DOCUMENTS

| | | | |
|---|---|---|---|
| 2005/0071143 | A1 | 3/2005 | Tran et al. |
| 2007/0259363 | A1 | 11/2007 | Amri et al. |
| 2009/0292482 | A1 | 11/2009 | Frumkin et al. |
| 2011/0098193 | A1* | 4/2011 | Kingsmore .......... C12Q 1/6869 506/9 |
| 2014/0100121 | A1 | 4/2014 | Lo et al. |
| 2015/0072865 | A1 | 3/2015 | Rubben |
| 2015/0197815 | A1 | 7/2015 | Kural |
| 2016/0058853 | A1 | 3/2016 | Sahin et al. |

FOREIGN PATENT DOCUMENTS

| | | |
|---|---|---|
| JP | 2015-513392 | 5/2015 |
| JP | 6403923 B1 | 10/2018 |
| JP | 2018-533113 A | 11/2018 |
| JP | 2019-3684 A | 1/2019 |
| KR | 10-2018-0090776 A | 8/2018 |
| KR | 10-2019-0028821 A | 3/2019 |
| WO | 2014/058987 A1 | 1/2005 |
| WO | 2006/103659 A2 | 10/2006 |
| WO | 2014-152990 A1 | 9/2014 |
| WO | 2017/035400 A1 | 3/2017 |
| WO | 2017/035400 A4 | 3/2017 |

OTHER PUBLICATIONS

Heng Li et al., Mapping short DNA sequencing reads and calling variants using mapping quality scores, Mar. 7, 2008, Cold Spring Harbor Laboratory Press, pp. 1851-1858 (Year: 2008).*

Cong-Jian Chen et al., ncPRO-seq: a tool for annotation and profiling of ncRNAs sRNA-seq data, Oct. 7, 2012, Published by Oxford University Press, vol. 28 No. 23 2012, pp. 3147-3149 (Year: 2012).*

Yachida et al., "Distant Metastasis Occurs Late During the Genetic Evolution of Pancreatic Cancer", Nature, vol. 467, No. 7319, Oct. 28, 2010 pp. 1114-1117.

Hong et al., "Tracking the Origins and Drivers of Subclonal Metastatic Expansion in Prostate Cancer" Nature Communications, vol. 6, No. 1, Apr. 1, 2015.

ISA/KR, International Search Report and Written Opinion, completed Dec. 21, 2016 for PCT Application No. PCT/US2016/048778, 15 pages.

Otsu Nobuyuki, "A Threshold Selection Method from Gray-Level Histograms", IEEE Transactions on Systems, Man, and Cybernetics, Jan. 1, 1979, vol. 1, No. 1, pp. 62-66 (Cited from Specification).

Li et al., "The Sequence Alignment/Map format and SAMtools", Bioinformatics, 2009, vol. 25, No. 16, pp. 2078-2079 (Cited from Specification).

Cibulskis et al., "Sensitive detection of somatic point mutations in impure and heterogeneous cancer samples" Nature Biotechnology, Mar. 2013,, vol. 31, No. 3, 9 pages (Cited from Specification).

Forbes et al., "COSMIC: mining complete cancer genomes in theCatalogue of Somatic Mutations in Cancer", Nucleic Acids Research, 2010, pp. 1-6 (Cited from Specification).

Huang et al., "Highly Recurrent TERT PromoterMutations in Human Melanoma", Science, Feb. 22, 2013, vol. 339, pp. 957-959 (Cited from Specification).

Larson et al., "SomaticSniper: identification of somatic point mutations in wholegenome sequencing data", Bioinformatics, 2012, vol. 28, No. 3, pp. 311-317 (Cited from Specification).

Li et al., "Mapping short DNA sequencing reads and calling variants using mapping quality scores", Genome Research, 2008, vol. 18, pp. 1851-1858 (Cited from Specification).

International Preliminary Report received for PCT Application Serial No. PCT/US2016/048778, dated Nov. 28, 2017, 16 pages.

Examination Report received in Australian Patent Application No. 2016310501, dated Mar. 29, 2019, 2 pages.

Office Action received in Canadian Patent Application Serial No. 2996704, dated Mar. 26, 2018, 5 pages.

Extended European Search result received in U.S. Patent Application Serial No. 16840158.6, Sep. 12, 2018, 10 pages.

Notice of Reasons for Refusal received for Japanese Patent Application Serial No. 2018-510329, dated Jul. 17, 2018, 6 pages (Including English Translation).

Saunders et al., "Strelka: Accurate somatic small-variant calling from sequenced tumor-normal sample pairs", Bioinformatics Advance Access, May 10, 2012, 7 pages.

Decision to Grant a Patent received for Japanese Patent Application Serial No. 2018-510329, dated Aug. 21, 2018, 5 pages (Including English Translation).

Office Action received in Canadian Patent Application Serial No. 2996704, dated Nov. 5, 2018, 7 pages.

Office Action received in Israel Patent Application Serial No. 257728, dated Dec. 2, 2018, 5 pages.

Office Action received in Korean Patent Application Serial No. 1020197007215, dated Jan. 20, 2020, 8 pages.

Office Action received in Korean Patent Application Serial No. 1020187008045, dated Jan. 28, 2019, 3 pages (Including English Translation).

* cited by examiner

SYSTEMS AND METHODS FOR GENETIC ANALYSIS OF METASTASES

This application claims priority to U.S. provisional application with the Ser. No. 62/209,850, which was filed Aug. 25, 2015.

FIELD OF THE INVENTION

The field of the invention is computational analysis of genetic information of a primary tumor and its metastases, especially as it relates to genetic differentiation and phylogenesis of sub-populations in metastases and their genetic origin.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications noted herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

As in many other solid tumors, melanoma metastases often first present in the lymph nodes draining the area of the primary tumor, whereas distant metastases tend to appear later. The conclusion that melanoma follows a linear progression from primary tumor to regional to distant metastases has supported pre-emptive surgical removal of regional lymph nodes with curative intent. However, several observations suggested that distant metastases are seeded early, contemporaneously with regional metastases. Patients who undergo resection of lymph node basins harboring metastasis do not experience a significantly extended life expectancy. Furthermore, circulating melanoma cells were detected in the blood of 26% of patients who only have metastases detected regionally. Unfortunately, current determinations often fail to provide a more detailed insight into tumor dissemination and phylogeny, particularly where multiple metastases are present.

In one known method, as described in WO2014/058987 tumor clonality is determined from omics data using an allelic state diagram. While such analysis provides valuable insight into the clonal diversity of a tumor, and possibly even sub-clonal phylogeny, such analysis is generally not applicable to omics data from tumors and their metastases at different sites or time points.

Thus, there is still a need for improved systems and methods for computational analysis of genetic information of a primary tumor and its metastases, especially as it relates to genetic differentiation and phylogenetic analysis of sub-populations in metastases and their genetic origin.

SUMMARY OF THE INVENTION

The inventive subject matter is directed to systems and methods of analyzing omics data from a tumor and its metastases to determine phylogeny of the metastases. Preferably, analysis includes stringent determination and status of somatic single nucleotide variants in the tumor and metastatic samples, and classification of the somatic single nucleotide variants (SSNV) as a fully shared SSNV, a partially SSNV, a private SSNV, or an absent SSNV. So classified SSNVs then allow calculation of a phylogenetic profile for the primary tumor and its metastases.

In one aspect of the inventive subject matter, the inventor contemplates a method of determining phylogeny of a metastasis that includes a step of providing a plurality of respective nucleic acid sequences from a primary tumor, a first metastasis, a second metastasis, and non-tumor tissue of the same patient. In a further step, somatic SSNVs are determined for the primary tumor, the first metastasis, and the second metastasis relative to the nucleic acid sequences from non-tumor tissue of the same patient, and in yet another step, the status (e.g., 'present' or 'absent') for each SSNV is determined with respect to each of the nucleic acid sequences from the primary tumor, the first metastasis, and the second metastasis. Most typically, the status is then used to classify each SSNV into a class (e.g., fully shared, partially shared, private, or absent), and the classification is used to calculate a phylogenetic profile for the primary tumor, the first metastasis, and the second metastasis.

While not limiting to the inventive subject matter, it is typically preferred that the step of determining the SSNVs includes computation of likelihoods of all possible genotypes for the primary tumor, the first metastasis, and the second metastasis, for example, using an error probability model. Moreover, it is contemplated that the so determined SSNVs may be further filtered using one or more filtering criteria, particularly where the determined somatic single nucleotide variant is heterozygous. For example, filtering criteria include filtering by genotype quality, by somatic score, by mapping quality, by quality sum of mismatches, by average number of mismatches, by fractional distance to 3'-end, and/or filtering by mutant allele depth. In still further contemplated aspects, each of SSNVs class may requires presence of a minimum number of members (e.g., at least three) of SSNVs, and each of the SSNVs may need a minimum sequencing coverage (e.g., to establish a tumor variant percentage with a 99% confidence interval of <1).

Therefore, and viewed from another perspective, the inventors also contemplate a method of determining phylogeny of a metastasis that includes a step of informationally coupling an analysis engine to a sequence database, wherein the sequence database stores a plurality of nucleic acid sequences from a primary tumor, a first metastasis, a second metastasis, and non-tumor tissue of the same patient. In a further step, the analysis engine then determines SSNVs for the primary tumor, the first metastasis, and the second metastasis relative to the nucleic acid sequences from non-tumor tissue of the same patient, typically using determination of likelihood for a possible genotype using an error probability model. The analysis engine further identifies for each of the primary tumor, the first metastasis, and the second metastasis fully shared SSNVs, partially shared SSNVs, private SSNVs, and absent SSNVs, and calculates a phylogenetic profile for the primary tumor, the first metastasis, and the second metastasis based on the fully shared SSNVs, partially shared SSNVs, private SSNVs, and absent SSNVs.

In particularly contemplated aspects, the nucleic acid sequences may be exome nucleic acid sequences or whole genome nucleic acid sequences, and/or may be in SAM or BAM format. Moreover, it is generally contemplated that the step of determining somatic single nucleotide variants comprises a step of computing likelihoods of all possible genotypes for the primary tumor, the first metastasis, and the second metastasis. The so determined SSNV may then be subject to further filtering, especially where the determined somatic single nucleotide variant is heterozygous. Suitable filters include filtering by genotype quality, by somatic score, by mapping quality, by quality sum of mismatches, by average number of mismatches, by fractional distance to 3'-end, and/or filtering by mutant allele depth. In addition, it is contemplated that the methods presented herein may also include a step of determining the allelic state for the somatic single nucleotide variants, and/or a step of determining a copy number aberration.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
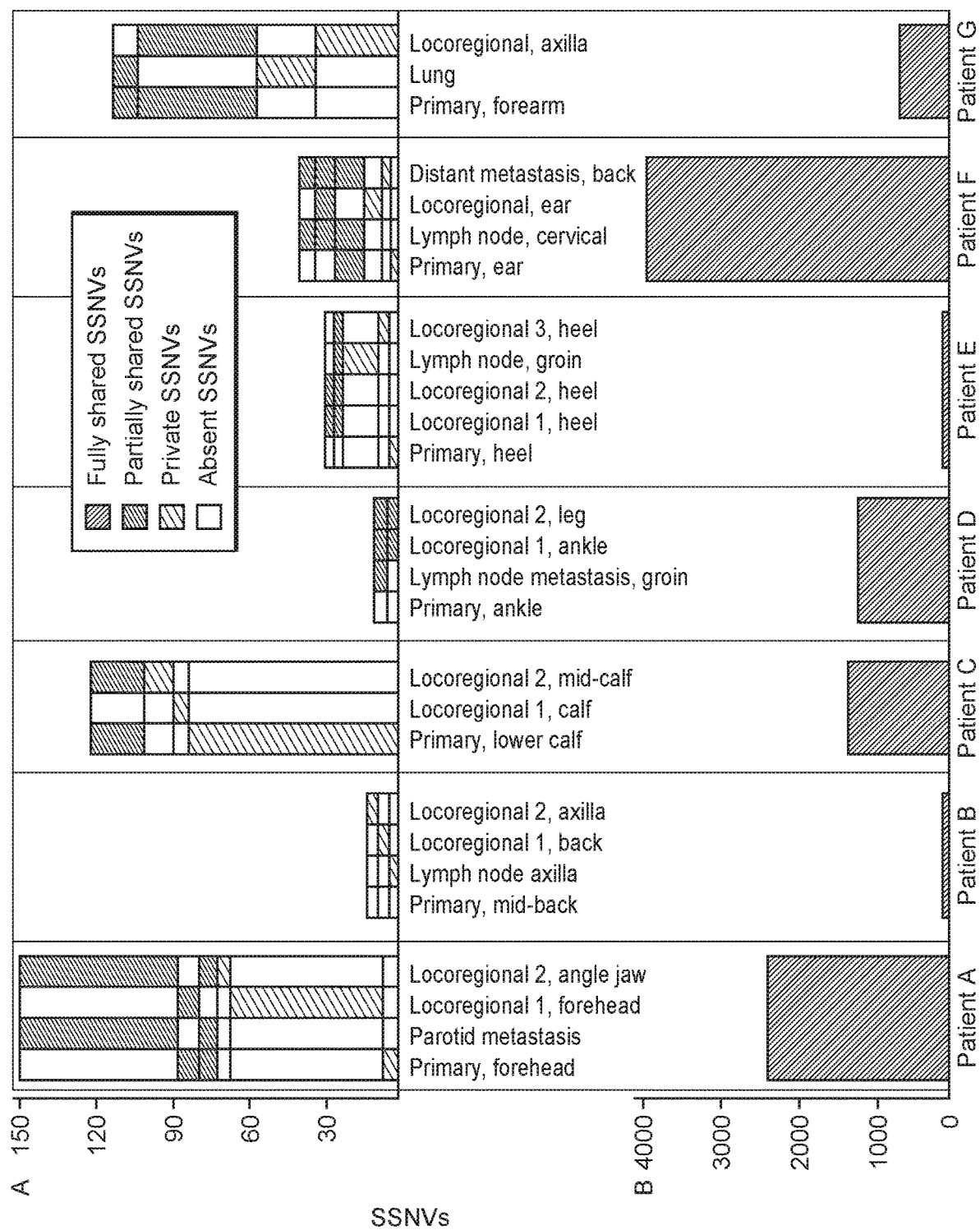
FIG. 1 exemplary shows status of SSNVs in primary tumors and their metastases from different patients.

Melanoma, like other cancers, appears to arise and evolve through the accumulation of genetic alterations within tumor cells. Comparing somatic mutations in a primary tumor and regional and distant metastases from the same patient can therefore provide insight into the phylogenetic relationships between distinct tumor cell populations and the order of metastatic dissemination. Such analyses may also provide answers to the question whether cells in the primary tumor that metastasize have acquired an ability to disseminate and seed other anatomic sites via new genetic alterations, or whether metastatic colonization is simply a stochastic process of which all cells in the primary tumor are capable, but few succeed.

Using whole-exome sequencing for discovery, and targeted sequencing for validation, the inventor analyzed mutation patterns of primary melanomas and two or more metastases in each of eight patients to determine their phylogenetic relationships. By sequencing tumor samples from patients with metastatic melanoma never subjected to targeted therapies, the inventor was able to trace the genetic evolution of cells in the primary tumor that seed metastases. The inventor was also able to show that distinct cells in the primary tumor depart multiple times in parallel to seed metastases, often after evolving from a common, parental cell subpopulation. Notably, the inventor also discovered that single metastases can be founded by more than one cell population found in the primary cancer. These mechanisms show how profound genetic diversity arises naturally among multiple metastases, driving growth and drug resistance, but also indicate certain mutations may distinguish cells destined to metastasize.

In one exemplary method of determining phylogeny of metastases, primary tumor samples and metastases are collected from a patient and typically fresh frozen or directly subjected to nucleic acid extraction. While in most cases genomic and/or exome analysis is preferred, additional or similar information may also be obtained from RNA sequencing. Nucleic acid isolation will generally follow known protocols. Likewise, sequencing can be performed in numerous manners, however, high-throughput and next generation sequencing is especially preferred. Consequently, nucleic acid sequences will be obtained from the primary tumor, a first metastasis, a second metastasis, and typically also non-tumor tissue of the same patient to identify patient specific single nucleotide variants. Of course, it should be noted that the sequence data may be in various formats, including FASTA, SAM, BAM, GAR, or a raw format, etc., and may be paired-end reads or single reads. Moreover, it should be appreciated that the sequence reads may be further processed (e.g., in an aligner, or by a user adding metadata), used directly from a sequencing device, or stored after optional in a database or other data carrier.

In a next step, SSNV are then determined, preferably by computing likelihoods of all possible genotypes for the primary tumor, the first metastasis, and the second metastasis. To obtain the most accurate results, SSNVs are typically calculated using a error probability model and one or more stringent filtering processes as is further described in more detail below. Upon filtering, status for each SSNV of a patient is then determined with respect to the primary tumor and each of the metastases using further conditional filters, and the status is then used to classify the SSNVs in to various groups (i.e., fully shared SSNV, partially shared SSNV, private SSNV, absent SSNV).

It should be particularly appreciated that such method uses a large quantity of highly complex and difficult to interpret data and simplifies these data with high accuracy to the most likely configuration in the genome or exome, and as such substantially facilitates tracing back phylogeny as is further described below. Of course, such systems are generally used in the context of a computing environment as the analysis as described herein cannot be done by a human in the course of a lifetime. Moreover, it should be noted that contemplated systems and methods presented herein substantially increase data processing speed and accuracy over other alignment and analysis methods, and therefore improve functioning and outcome of computer driven analysis of SSNVs.

It should be noted that any language directed to a computer or computing device should be read to include any suitable combination of computing devices, including servers, interfaces, systems, appliances, databases, agents, peers, engines, controllers, modules, or other types of computing devices operating individually, collectively, or cooperatively. One should appreciate the computing devices comprise one or more processors configured to execute software instructions stored on a tangible, non-transitory computer readable storage medium (e.g., hard drive, FPGA, PLA, solid state drive, RAM, flash, ROM, etc.). The software instructions specifically configure or program the computing device to provide the roles, responsibilities, or other functionality as discussed below with respect to the disclosed apparatus. Further, the disclosed technologies can be embodied as a computer program product that includes a tangible, non-transitory computer readable medium storing the software instructions that causes a processor to execute the disclosed steps associated with implementations of computer-based algorithms, processes, methods, or other instructions. In some embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges among devices can be conducted over a packet-switched network, the Internet, LAN, WAN, VPN, or other type of packet switched network; a circuit switched network; cell switched network; or other type of network.

As used in the description herein and throughout the claims that follow, when a system, engine, server, device, module, or other computing element is described as configured to perform or execute functions on data in a memory, the meaning of "configured to" or "programmed to" is defined as one or more processors or cores of the computing element being programmed by a set of software instructions stored in the memory of the computing element to execute the set of functions on target data or data objects stored in the memory.

Therefore, and viewed from a different perspective, the inventor contemplates that an analysis engine can be informationally coupled to a sequence database or one or more sequencing devices that store or provide a plurality of nucleic acid sequences from a primary tumor, a first metastasis, a second metastasis, and non-tumor tissue of the same patient. The analysis engine then determines SSNVs for the primary tumor, the first metastasis, and the second metastasis relative to the nucleic acid sequences from non-tumor tissue of the same patient, preferably using an error probability model as is further described in more detail below. The analysis engine then identifies, for each of the primary tumor, the first metastasis, and the second metastasis fully shared SSNVs, partially shared SSNVs, private SSNVs, and absent SSNVs, and calculates a phylogenetic profile for the primary tumor, the first metastasis, and the second metastasis based on the fully shared SSNVs, partially shared SSNVs, private SSNVs, and absent SSNVs.

Using the above methods and systems, and as also provided in more detail below, the inventor performed whole-exome sequencing of primary melanomas and multiple matched metastases from eight patients to elucidate their phylogenetic relationships. In 6 of 8 patients, the inventor found that genetically distinct cell populations in the primary tumor metastasized in parallel to different anatomic sites, rather than sequentially from one site to the next. In 5 of these 6 patients, the metastasizing cells had themselves arisen from a common parental subpopulation in the primary tumor, indicating that the ability to establish metastases can be a late-evolving trait. Interestingly, the inventor also discovered that individual metastases were sometimes founded by multiple cell populations of the primary tumor that were genetically distinct. Such establishment of metastases by multiple tumor subpopulations could help explain why identical resistance variants are identified in different sites after initial response to systemic therapy. For example, one primary tumor harbored two subclones with different oncogenic mutations in CTNNB1, which were both propagated to the same metastasis, raising the possibility that activation of WNT signaling may be involved, as has been suggested by experimental models.

EXAMPLES

Study design and tumor samples: Tumor samples were obtained from 1) the Melanoma Institute Australia (MIA) Biospecimen Bank, a prospective collection of fresh-frozen tumors accrued with informed consent and IRB approval since 1996 through MIA (formerly the Sydney Melanoma Unit); and 2) the Tumor Procurement Service of Memorial Sloan-Kettering Cancer Center (MSKCC), a biospecimen collection of fresh-frozen tumors acquired and managed in accordance with requirements stipulated by the Institutional Review Board and the Human Biospecimen Utilization Committee of MSKCC. Tumors were included from patients for whom primary melanomas and two or more metastases were available. No samples were excluded during the course of the study. There were no additional exclusion criteria.

The patients with lymph node metastases at time of initial presentation and staging (SLNB) were B, D, E, and F. Where multiple positive lymph nodes were detected, only one was taken for sequencing. These patients were profiled before the advent of targeted therapeutics and were not given interferon or any systemic chemotherapies before the tumors were banked.

Banked fresh-frozen tumor metastasis samples selected for analysis were reviewed by a pathologist and scored for the percentage of tumor cells present and necrosis. Linked pathologic data were obtained for number of nodes involved, largest metastasis size and presence of extranodal spread.

DNA isolation and sequencing: At least 5 micrograms of DNA from dissected tissue and matching DNA from peripheral blood were extracted using the DNeasy kit (Qiagen) and the Flexigene kit (both Qiagen), respectively. For sequencing, approximately 1.0 μg genomic DNA from tumor and normal tissue was sheared by sonication to an average length of 150 bp on a Covaris E220 acoustic sonicator. About 71 megabases of coding sequence and untranslated regions were targeted using oligonucleotide-based hybrid capture using Agilent SureSelect Exome Capture kits with the v4 exome+UTR bait library. Sequencing-by-synthesis using the Illumina HiSeq2000 systems resulted in more than 85% of targeted regions receiving 150× fold coverage at >90% of bases.

Somatic single nucleotide variant (SSNV) calling: Raw sequencing data in Illumina's FASTQ data format was converted into FASTQ files with base quality scores encoded in the Sanger basecall format. Next, the reads were aligned using the BWA aligner (*Genome Res* 18(11):1851-1858) This aligner is based on the Burrows-Wheeler transformation, aligns paired-end reads and handles indels robustly. The output of BWA are the aligned reads in SAM format (currently standard file format for aligned sequence data). Reads stored in SAM format were then converted to the binary BAM format using the samtools software (*Bioinformatics* 25(16):2078-2079). Once reads were in the sorted and indexed BAM file format, position based retrieval of reads was expedited and data storage requirements were minimized. Next, to remove erroneous mutation calls due to PCR duplication, all duplicate reads were removed using MarkDuplicates, an analysis tool included in the Picard software package developed by the Broad Institute (URL: sourceforge.net/projects/picard/). After removal of the duplicate reads, the base quality scores were recalibrated using the CountCovariates and TableRecalibration tools included in the GATK software, also developed by the Broad Institute (URL: www.broadinstitute.org/gatk/#Introduction).

The tumor and matched normal BAM files were analyzed for single nucleotide variants with the following method. Sequenced bases with ≥8 unique (non-duplicate reads) with mapping quality ≥20 in both tumor and matched normal were used to compute the likelihoods of all possible genotypes (AA, AT, AC, etc.) using the MAQ error model. In this context, it is noted that some of the new sequencing technologies produce very short reads that effectively require new algorithms to process. In particular, substantial problems are encountered in efficiently aligning short reads to a reference genome and handling ambiguity or lack of accuracy in this alignment. To that end, error models are particularly advantageous where mapping quality (a measure of the confidence that a read actually comes from the position it is aligned to by the mapping algorithm) is taken into account. For example, MAQ can build assemblies by mapping shotgun short reads to a reference genome, using quality scores to derive genotype calls of the consensus sequence of a diploid (human) genome. MAQ makes full use of mate-pair information and estimates the error probability of each read alignment. Error probabilities may be derived for the final genotype calls, most preferably using a Bayesian statistical model that incorporates the mapping qualities, error probabilities from the raw sequence quality scores, sampling of the two haplotypes, and an empirical model for correlated errors at a site. For example, a suitable Bayesian statistical model is available in the samtools source code. If less than two reads support any non-reference allele at the current position, then that the position was deemed homozygous reference and no further analysis was performed.

The genotype likelihoods were used in a Bayesian model used by the Somatic Sniper method (*Bioinformatics* 28(3): 311-317), incorporating a prior probability on the reference, the fraction of heterozygous positions in the human genome, the probability to convert the normal genotype to the tumor genotype. Each tumor/normal genotype pair was scored using this model. The genotype pair with the highest likelihood given the data was chosen as the most likely tumor and normal genotypes. Any position determined to be homozygous for the reference allele in both tumor and normal was not further analyzed.

If tumor and normal genotypes were identical, the variant was classified as germline. Instances where the normal genotype was heterozygous and the tumor genotype was homozygous suggest regions of loss-of-heterozygosity (LOH), and such variants were so classified. For variants classified as either germline or LOH, the log-likelihood of the paired genotype was used to compute a Phred-scaled quality/confidence of the germline variant. All other variants were classified as a somatic mutation and their Somatic Score (SS) was calculated.

For any position where the tumor and/or normal genotype was not homozygous for the reference allele, a number of metrics were computed, including number of total reads, number of allelic reads, average base and mapping quality, number of reads with mapping quality=0, number and quality sum of mismatches in reads with variant or reference allele, the distance of the variant to the 3' end of the read, and number of reads aligned to the forward/reverse strand. All putative variants and their associated metrics were converted to the VCF format and the following filters (*Bioinformatics* 28(3):311-317) applied: conf: Genotype quality or Somatic Score≥100; dp: Total depth (DP of normal+primary)≥8; mq0: # number of mapping quality=0 reads<5; sb: Mutant allele strand bias p-value>0.005. (Binomial test); mmqs: quality sum of mismatches (per read)≤20; amm: average number of mismatches (per read)≤1.5; detp: fractional distance to 3'<0.2 or >0.8; ad: mutant allele depth in tumor≥4; gad: mutant allele depth in normal≤3; and ma: Only two alleles at position have read support≥2.

Variants that passed all above filters were marked PASS in the filter column of their VCF record. Otherwise, the names of each filter that the variant failed was recorded instead. A single VCF file was produced for each tumor sample (i.e., primary tumor or metastasis).

SSNV calling using the present method compared to mutect: A cross-validation of the variant analysis pipeline was performed using the Broad's Mutect (*Nat Biotechnol* 31(3):213-219) calls for a single series (one primary tumor and three metastases from patient RPA08-0209). Mutect was run in its default configuration using the patient's matched normal as a control. The filtered sets of variant calls made by Mutect for each tumor vs. matched normal were then post-processed identically to the variant calls made by the variant caller presented herein, classifying each identified variant as FULLY SHARED (present in all samples), PRIVATE (present in only one sample), or otherwise found in more than one, but not all samples. The categorized sets of variant calls for the RPA08-0209 series made by Mutect were then campated with the variant calls established by the methods presented herein.

Overall, 2,301 variants were found in both sets in identical categories. An additional 732 variants were exclusive to Mutect's set and 229 variants were exclusive to present method. Out of the 732 variants exclusive to Mutect's set, there were 617 FULLY SHARED variants (84%), 105 PRIVATE variants (14%), and an additional 10 variants present in other sample combinations (1%). Out of the 229 variants exclusive to the present method, 208 were classified as FULLY SHARED (91%), 10 were classified as PRIVATE (4%), and 11 were found in other sample combinations (5%). Notably, when investigated why some of the variants found in Mutect's set were not called in the present method, it was found that of the 617 FULLY SHARED variants in Mutect's set, 611 variants were called by present method but filtered out. Two filters, MMQS and AMM, were responsible for filtering out the majority of these calls. These filters discard variants located on sequencing reads with a high number of other mismatched bases, attempting to reduce the number of false positives induced by poor quality and/or reads that are aligned incorrectly. Of the 105 PRIVATE variants exclusive to Mutect's set, 88 were not called by present method (84%), while 17 were filtered out (16%). As expected, these 88 variants had low alternate allele frequencies, the inclusion of which is a major strength of Mutect's mutation model. However, as PRIVATE variants with low allele frequencies most likely arose late during the development of these tumors post-divergence, they provide limited information the phylogenetic analyses.

Indel calling was performed by Strelka (*Bioinformatics* 2012 Jul. 15; 28(14):1811-7) using default parameters except with its depth filter turned off as recommended for exome sequencing input data. All somatic indels called by Strelka were collected for each sample. The PRESENT/ABSENT status for each indel was then determined for samples in a patient series in a manner identical to how substitution SSNVs were handled, as described above.

Classification of SSNV detection states in individual patients: All variants discovered in any of the samples from a given patient were combined to determine whether that variant was present in all samples. Variants that failed one or more filters in all samples of the series were removed. For variants that were marked PASS in at least one sample of a series, sample-specific metrics of the variant were collected for all samples in the series, including overall read depth, reference and alternate allele depths, failed filters (if any), as well as general information of the variant such as protein change, variant classification, and the number of samples in the COSMIC database that have a mutations at the same position (Release v55 (*Nucleic Acids Res* 39(Database issue):D945-950)). The filter criterion of ≥8 unique reads listed above allowed for the possibility that variants present in low fraction in one of the samples in a series could be missed. To account for this possibility, the reference and alternate allele read depths for all samples including the matched normal of the series were updated using the raw sequencing data in each sample's BAM file, tallying the number of reference and alternate alleles with base quality≥20.

Based on the stringent PASS designation detailed above for individual variants, each somatic variant was then classified as PRESENT or ABSENT for each sample of a patient. A variant was classified as PRESENT if 1) it was called PASS in the sample or 2) if it was detected at any depth in the sample's raw sequencing data AND called PASS in at least one other sample in the same patient. A variant was classified ABSENT if called PASS in at least one other sample in the same patient, but lacking any evidence in raw sequencing data for the sample in question. Somatic variants classified as PRESENT in all samples of a patient were further classified as FULLY SHARED, if all tumors in that patient shared these variants, indicating that they derived from a common ancestor cell, harboring that variant. All other variants were classified as NON-FULLY SHARED, indicating that they reside on a later-arising evolutionary branch.

Classes of SSNVs with identical PRESENT/ABSENT status across all samples in a patient were further analyzed regarding phylogenetic relationships between samples. To focus on classes supported by the greatest evidence, the following was required 1) at least 3 SSNVs per class and 2) each member SSNV has sufficient sequencing coverage to establish a TVP with a 99% confidence interval of <1 (e.g., given the mean normal cell contamination across all samples, this threshold was ≥42 reads after elimination of duplicates). It was further observed that weakly supported variant calls (e.g., total read depth<42 reads in all tumors and matched normal) tended to be found in poorly-captured or off-target regions of the genome, further justifying their exclusion.

The number of SSNVs that met these thresholds and were classified into classes as are shown in FIG. 1 and Table 1 below. In FIG. 1, evolutionary divergence during metastatic dissemination is exemplarily illustrated. For the seven of eight patients also yielding high-confidence copy number estimates, the number of SSNVs in each tumor tissue are shown. The number of fully shared SSNVs present in all tumors is displayed in the bottom column graph. The number of SSNVs not present in all samples is shown in the upper column graph. The SSNVs not present in all samples are further subdivided for each sample into tiers of SSNVs: those that are partially shared with other tumors (dark grey), those that are private to the sample (present only in one sample of a patient, light grey), and those not detected in the sample (white). Tiers with fewer than 3 SSNVs are not displayed. P denotes present, A denotes absent, with location indicated in parentheses.

| Patient | Class | Pattern | SSNV # | Discussion |
|---|---|---|---|---|
| A | 1 | P(prim) P(parotid) P(Ir1 forehead) P(Ir2 jaw) | 2323 | Fully shared |
| A | 2 | P(prim) P(parotid) A(Ir1 forehead) P(Ir2 jaw) | 7 | Deleted SSNVs on chromosome 13 in locoregional 1 forehead |
| A | 3 | P(prim) A(parotid) P(Ir1 forehead) A(Ir2 jaw) | 8 | SSNVS present in the primary and locoregional 1 forehead, but absent in the parotid and locoregional 2 jaw metastases |
| A | 4 | P(prim) A(parotid) A(Ir1 forehead) A(Ir2 jaw) | 5 | Private (primary) |
| A | 5 | A(prim) P(parotid) A(Ir1 forehead) P(Ir2 jaw) | 62 | SSNVS present in the parotid and locoregional 2 jaw metastases but absent in the primary and locoregional 1 forehead |
| A | 6 | A(prim) A(parotid) P(Ir1 forehead) A(Ir2 jaw) | 55 | Private (locoregional 1 forehead) |
| A | 7 | A(prim) A(parotid) A(Ir1 forehead) P(Ir2 jaw) | 5 | Private (locoregional 2 jaw) |
| A | N.A. | NA. | 282 | Classes with <3 total SSNVs or <42 sequencing reads in at least one sample |
| B | 1 | P(prim) P(In) P(Ir1 back) P(Ir2 axilla) | 86 | Fully shared |
| B | 2 | A(prim) P(In) A(Ir1 back) A(Ir2 axilla) | 3 | Private (lymph node) |
| B | 3 | A(prim) A(In) P(Ir1 back) A(Ir2 axilla) | 5 | Private (locoregional 1 back) |
| B | 4 | A(prim) A(In) A(Ir1 back) P(Ir2 axilla) | 4 | Private (locoregional 2 axilla) |
| B | N.A. | N.A. | 43 | Classes with <3 total SSNVs or <42 sequencing reads in at least one sample |
| C | 1 | P(prim) P(Ir1 calf) P(Ir2 r mid-calf) | 1288 | Fully shared |
| C | 2 | P(prim) A(Ir1 calf) P(Ir2 mid-calf) | 21 | Rare primary subclone, absent in locoregional 1 calf, present in locoregional 2 mid-calf |
| C | 3 | P(prim) A(Ir1 calf) A(Ir2 mid-calf) | 82 | Private (primary) |
| C | 4 | A(prim) P(Ir1 calf) A(Ir2 mid-calf) | 6 | Private (locoregional 1 calf) |
| C | 5 | A(prim) A(Ir1 calf) P(Ir2 mid-calf) | 12 | Private (locoregional 2 mid-calf) |
| C | N.A. | N.A. | 165 | Classes with <3 total SSNVs or <42 sequencing reads in at least one sample |
| D | 1 | P(prim) P(In) P(loc rec ankle) P(met leg) | 1150 | Fully shared |
| D | 2 | A(prim) P(In) P(loc rec ankle) P(met leg) | 4 | Rare variants seen both in LN and locoregional metastases |
| D | 3 | A(prim) A(In) P(loc rec ankle) P(met leg) | 5 | Rare variants seen only in locoregional metastases |
| D | N.A. | N.A. | 173 | Classes with <3 total SSNVs or <42 sequencing reads in at least one sample |

| Patient | Class | Pattern | SSNV # | Discussion |
|---|---|---|---|---|
| E | 1 | P(prim) P(Ir1) P(Ir2) P(In) P(Ir3) | 68 | Fully shared |
| E | 2 | P(prim) A(Ir1) A(Ir2) A(In) A(Ir3) | 3 | Private (primary) |
| E | 3 | A(prim) P(Ir1) P(Ir2) P(In) P(Ir3) | 3 | Primary subclone selected into metastases |
| E | 4 | A(prim) A(Ir1) A(Ir2) P(In) A(Ir3) | 14 | Private (lymph node metastasis) |
| E | 5 | A(prim) P(Ir1) P(Ir2) A(In) A(Ir3) | 3 | Possible rare subclone in locoregional metastases 1 and 2; too few to confirm |
| E | 6 | A(prim) A(Ir1) A(Ir2) A(In) P(Ir3) | 5 | Private (locoregional 3) |
| E | N.A. | N.A. | 52 | Classes with <3 total SSNVs or <42 sequencing reads in at least one sample |
| F | 1 | P(prim) P(In) P(Ir ear) P(distant skin met) | 3897 | Fully shared |
| F | 2 | P(prim) P(In) A(Ir ear) P(distant skin met) | 11 | Deleted SSNVs on chromosome 7 in locoregional ear |
| F | 3 | P(prim) A(In) A(Ir ear) A(distant skin met) | 3 | Private (primary) |
| F | 4 | A(prim) P(In) P(Ir ear) P(distant skin met) | 9 | Deleted SSNVs on chromosome 15 in primary |
| F | 5 | A(prim) P(In) A(Ir ear) P(distant skin met) | 6 | Small number of shared SSNVs indicating common, distinct parent of lymph node and distant skin metastasis back |
| F | 6 | A(prim) A(In) A(Ir ear) P(distant skin met) | 3 | Private (distant skin metastasis back) |
| F | 7 | A(prim) A(In) P(Ir ear) A(distant skin met) | 7 | Private (locoregional ear) |
| F | N.A. | N.A. | 1032 | Classes with <3 total SSNVs or <42 sequencing reads in at least one sample |
| G | 1 | P(prim) P(lung) P(Ir axilla) | 647 | Fully shared |
| G | 2 | P(prim) A(lung) P(Ir axilla) | 48 | X and chromosomes 1,8 and 16 loss in lung metastasis |
| G | 3 | P(prim) P(lung) A(Ir axilla) | 10 | Chromosome 7 loss in locoregional axilla |
| G | 4 | A(prim) A(lung) P(Ir axilla) | 32 | Private (locoregional axilla) |
| G | 5 | A(prim) P(lung) A(Ir axilla) | 23 | Private (lung metastasis) |
| G | N.A. | N.A. | 96 | Classes with <3 total SSNVs or <42 sequencing reads in at least one sample |
| H | 1 | P(prim) P(Ir leg) P(In) P(brain) | 122 | Fully shared |
| H | 2 | P(prim) P(Ir leg) P(In) A(brain) | 9 | Deleted SSNVS in deletions of different chromosomes in brain metastasis |
| H | 3 | P(prim) A(Ir leg) A(In) P(brain) | 6 | Deleted SSNVS in deletions of different chromosomes in locoregional leg and lymph node |
| H | 4 | P(prim) A(Ir leg) A(In) A(brain) | 24 | Private (primary) |
| H | 5 | A(prim) P(Ir leg) P(In) P(brain) | 5 | Primary subclone selected into metastases |
| H | 6 | A(prim) P(Ir leg) P(In) A(brain) | 35 | Possible subclone present only in locoregional leg and lymph node |
| H | 7 | A(prim) P(Ir leg) A(In) A(brain) | 27 | Private (locoregional leg) |
| H | 8 | A(prim) A(Ir leg) P(In) A(brain) | 1849 | Private (lymph node) |
| H | 9 | A(prim) A(Ir leg) A(In) P(brain) | 973 | Private (brain metastasis) |
| H | N.A. | N.A. | 569 | Classes with <3 total SSNVs or <42 sequencing reads in at least one sample |

Promoter mutations in TERT (*Science* 339(6122):957-959) were manually inspected—the C228T mutation was detected in tumors of patients F and G, and the C250T mutation was found in tumors of patients A, C, and D. The mutations were fully shared amongst all tumors of all patients, with the exception of the distant back metastasis of patient F, however only 20 reads covered this position, making it likely it was present but insufficiently sampled.

Ion torrent validation sequencing: From each sample, amplicons were pooled in equimolar amounts, 10-100 ng were input into the Ion Xpress Plus Fragment Library Kit. Sequencing template was generated using emulsion PCR on the Ion OneTouch 2 using the Ion PGM Template OT2 200 kit. Up to 12 barcoded samples were multiplexed on Ion 318 v2, or Ion 316 v2 chips. Sequencing was performed on a Personal Genome Machine (PGM) sequencer (Ion Torrent) using the Ion PGM 200 v2 sequencing kit. Torrent Suite software version 4.0.2 was employed to align reads to hg19. Reads were visualized using IGV v 2.2.32 (Broad Institute) and variant allele frequencies were determined for sites previously identified via Illumina sequencing.

Calling of copy number aberrations (CNAS): For copy number aberrations/variants, referred to here as CNAs, average tumor vs. matched normal relative coverage and standard deviation were calculated for each captured exon by dividing read depth measured in the tumor by the read depth in the matched normal for each position within the exon. Exons that were insufficiently covered (average read depth<5 reads) in both tumor and matched-normal were removed from the remaining analysis. Average relative coverage was corrected for GC bias using LOWESS regression. The average majority allele fraction in both tumor and matched normal was computed for exons with at least one heterozygous SNP in the normal tissue:

$$AF_m^t = \frac{DP_{major}^t}{DP_{total}^t}, AF_m^n = \frac{DP_{major}^n}{DP_{total}^n}$$

Where $DP_{major}^t$ and $DP_{major}^n$ are the read depths of the germline allele with the greatest read support and $DP_{total}^t$ and $DP_{total}^n$ are the total read depths at the position in the tumor and matched normal, respectively. Relative coverage is determined simply by dividing the coverage observed in tumor by the matched-normal's coverage, i.e., $RC=DP_{total}^t/DP_{total}^n$. The standard deviation of $AF_m$ estimates was computed for exons featuring at least three heterozygous SNPs.

To determine CNAs, the exon-level statistics computed above were iteratively aggregated into larger segments in an agglomerative process similar in spirit to hierarchical clustering. In the first round, every pair of neighboring exons was analyzed. Neighboring exons that did not have significantly different relative coverage and $AF_m^t$ (only for exons with heterogeneous SNPs) estimates (p>0.999, two-sample Student's t-test) were merged into a single segment. The average relative coverage and $AF_m^t$ for the new segment were calculated as the base-pair count adjusted averages and standard deviations of the two individual exons measurements. This procedure was continued with neighboring segments using the same method. When no more segments could be merged, then any segment or exon with fewer than 1,000 reads and/or 10 heterozygous SNPs, were removed as their weak statistics may be impeding their immediate neighbors from being merged together. After culling these segments and exons, another round of iterative merging was performed, combining any newly neighboring segments that were compatible, until no more compatible segments remained. The relative coverage estimates of all segments were centered to the median of the entire genome, which was assigned the value of 1.0, signifying the normal copy number state. A skew in $AF_m^t$ estimates caused when the majority allele's read support arose from sampling bias instead of an underlying imbalance in allele copy number was corrected by subtracting out the $AF_m^n$ estimated in the matched normal sample. However, because such sampling bias only occurs in regions in which both alleles have roughly equal copy number, the correction was made using the following equation:

$$AF_{m,corr}^t = AF_m^t - (AF_m^n - 0.5)e^{-0.5\left(\frac{AF_m^t - AF_m^n}{0.05}\right)^2}$$

The corrected set of segments and exons were then manually reviewed to search for larger regions of contiguous segments with similar relative coverage and $AF_{m,corr}^t$ estimates, indicating that all contiguous segments share the same allelic state. For region j, the region's relative coverage and allele fraction is defined as the average of all segments' estimates within the region, hereafter referred to as $RC_{obs}^j$ and $AF_{obs}^j$.

Determining allelic states from relative coverage and allele fraction: An integral allelic state, such as diploid (1,1) or single copy gain (2,1), will have an expected copy number CN (2 and 3 for the two preceding examples), and allele fraction AF (50/50 and 66.6/33.3 for the two preceding examples) for a given allelic state i based on the following equations:

$$CN_{exp}^i(t_{maj}^i, t_{min}^i, n_{maj}, n_{min}, \alpha) = \frac{(1-\alpha)(t_{maj}^i + t_{min}^i) + \alpha(n_{maj} + n_{min})}{n_{maj} + n_{min}}$$

$$AF_{exp}^i(t_{maj}^i, t_{min}^i, n_{maj}, n_{min}, \alpha) = \frac{(1-\alpha)t_{maj}^i + \alpha n_{maj}}{(1-\alpha)(t_{maj}^i + t_{min}^i) + \alpha(n_{maj} + n_{min})}$$

where $t_{maj}^i$, $t_{min}^i$ are the copy numbers of the majority and minority alleles for the i-th allelic state in the tumor, $n_{maj}$, $m_{min}$ are the copy numbers of each allele in the matched-normal samples (assumed to be diploid, $n_{maj}=m_{min}=1$), and α is the fraction of normal contaminant the tumor sample.

To determine the allelic state most likely to produce the observed relative coverage and allele fraction estimates, three parameters were determined that transform the observed data to the expected values of copy number and allele fraction from the set of possible allelic states. The three parameters are as follows: fraction of normal contamination α, relative coverage delta d, and relative coverage scaling factor s. The α parameter controls the expected estimates for $CN_{exp}^i$ and $AF_{exp}^i$, while the latter two parameters transform the observed estimates of relative coverage. The parameters d and s affect the y-axis shift and scale of a segment's relative coverage estimate from the diploid allelic state (1,1) according to the following equation:

$$CN_{obs}^j(RC_{obs}^j, d, s) = s(RC_{obs}^j - d) + 1.0$$

where $RC_{obs}^j$ is observed relative coverage and $CN_{obs}^j$ is the observed relative copy number of segment j.

The optimal values for these three parameters were discovered using a Gradient Steepest Descent Search to find the minimum root mean square deviation (RMSD) across all regions for a tumor sample. The minimal deviation of region j was determined by comparing $CN_{obs}^j$ and $AF_{obs}^j$ to the expected values of the closest allelic state:

$$m^j = \min_i\left[(CN_{obs}^j - CN_{exp}^i)^2 + (AF_{obs}^j - AF_{exp}^i)^2\right]$$

The allelic state i ($t_{maj}^i$, $t_{min}^i$) that produces the minimal deviation was recorded as the most likely allelic state for region j given the current parameter set. The RMSD of all regions was then computed as the square root of the sum of all regions' minimal deviations weighted by their genomic widths, $w_j$, to normalize the influence of shorter regions relative to larger regions on the RMSD computation:

$$RMSD = \sqrt{\frac{\sum_j w^j m^j}{\sum_j w^j}}$$

The search began with a set of initial values for each parameter (d=0, s=2, and α=0.1), and a set of increments for each parameter, $d_x$, $s_x$, and $\alpha_x$ (d ranged from 0 to 1 in increments of 0.2 (5 steps), s ranged from 0.5 to 4 in increments of 0.5 (5 steps), and α ranged from 0.1 to 0.9 in increments of 0.2 (4 steps)). For each parameter, p, and parameter increment, $p_x$, the RMSD was calculated for p, $p+p_x$, and $p-p_x$. The parameter value that yields the greatest reduction in RMSD was chosen as the new current value for that parameter. The current values of all parameters and their incremented counterparts were used to calculate a new set of RMSDs from which the next update to a parameter's value was selected, and so on. If no reduction in RMSD was possible with the current parameter increments (i.e. the current values of the three parameters have the lowest RMSD), then each increment was divided half and the search resumes. After three rounds of such parameter divisions, the search was concluded and the final values of the three parameters were recorded as the best fit parameters. Since gradient descent searches can fall into local minima, the gradient search process was performed multiple times with different initial parameters until a consistent set of fit parameters was converged upon. Then, in a manual process, the expected and observed estimates using the final set of parameters were compared to determine whether or not the gradient search found a good solution.

If a consistent set of fit parameters could not be determined after numerous parameter initializations, or if the best fit parameters failed to properly model the observed data upon manual review, the three parameters were manually adjusted until a reasonable fit was found. A total of 5×5×4=100 starting points were used.

The inventors used an interactive web-based tool that graphs the relative coverage and allele fraction estimates for all segments on a scatter plot, correcting relative coverage using the best fit values for d and s. The position of several allelic states (e.g. (1,1), (2,1), (2,0), etc.) were overlaid on this graph after adjusting their positions by the best fit values for alpha. The positions of the allelic states were compared to the clusters of segments to see if large clusters overlap the position of an allelic state. The observed data was "properly" modeled by the fitted parameters when all or most large clusters center around an allelic state. If many large clusters were not found on an allelic state, the interactive tool was used to adjust the parameters d, s, and α to see if a better fit could be determined manually.

The finalized set of parameters was used to determine the closest allelic state for each region j in the manner described above. Regions with observed copy number and allele fraction estimates that place them in between two allelic states indicated that they were "potentially" subclonal based on their relative coverage and allele fraction, which was then verified or nullified via the TVP estimates described in more detail below. The precise mixture of allelic states was determined with the method described below.

Determining total unique copy number variants found in each patient: For each curated segment, a unique set of all copy number states was identified for all tumor samples in the patient. If a region was subclonal in a sample, then the two integral copy number states that can be combined to produce the observed copy number state were added to the set. The unique set of copy number states was then deduced. Because FISH analysis (below) supported a predominantly (1,1) diploid state in A-G, if a (1,1) allelic state was detected, it was deduced that that region harbored no copy number variants. If all samples shared an identical aberrant state (i.e. other than (1,1)), that variant was determined to be FULLY SHARED. All other remaining copy number states, those demonstrating copy number aberrations in some but not all samples, were defined as NON-FULLY SHARED. The number of FULLY SHARED, NON-FULLY SHARED states, as well as total number of samples with subclonal allelic states, were tallied for each curated segment.

Calculation of tumor variant percentage (TVP) and 99% confidence intervals for SSNVs: The inventors sought to calculate proportion of tumor cells in a sample that contained each SSNV (TVP). In contrast, the allele frequency of a mutation is the proportion of all DNA strands that contained each SSNV, with higher copy number and normal contamination affecting that proportion. It is therefore necessary to translate the proportion of DNA strands containing a SSNV into the proportion of tumor cells containing the strand. A principled statistical approach to determine this proportion required an estimate of the normal cell contamination of the sample, the copy number state at the SSNV, and the number of reads of its reference and mutant allele.

To calculate the TVP it was assumed that there are two populations of tumor cells, A and B, with the proportion of tumor cells coming from population A being the Tumor Variant Proportion (TVP). It was also assumed that each population is homogeneous so that for all cells in population A there are $A_{Total}$ strands (or copies) of DNA covering the SSNV location and $A_{Mut}$ of these strands contain the SSNV. $B_{Total}$ and $B_{Mut}$ for the B population were similarly defined. Then with no normal contamination one can write the allele frequency of the SSNV as $$AF_{Tumour} = \frac{A_{Mut}TVP + B_{Mut}(1-TVP)}{A_{Total}TVP + B_{Total}(1-TVP)}$$

With normal contamination, α proportion of the cells are normal cells each of which contributes 2 strands of DNA and, by assumption, do not contain the SSNV. In this case the allele frequency of the SSNV become $$AF = \frac{[A_{Mut}TVP + B_{Mut}(1-TVP)](1-\alpha)}{[A_{Total}TVP + B_{Total}(1-TVP)](1-\alpha) + 2\alpha}$$

When inverted this equation to solve for the TVP $$TVP(AF, \alpha, A_{mut}, B_{mut}, A_{total}, B_{total}) = \\ \frac{(1-\alpha)B_{mut} - AF[2\alpha + (1-\alpha)B_{total}]}{AF(1-\alpha)(A_{total} - B_{total}) - (1-\alpha)(A_{mut} - B_{mut})}$$

However, when searching for subclonal SSNVs, by definition, one is interested only in those mutations that are found in one clone but not the other, so in these specific instances, either $B_{mut}=0$ or $A_{mut}=0$. To simplify the analysis, only regions in which the two populations, A and B, have the same total copy number status were considered, so that $A_{total}=B_{total}$ and one could assume that $A_{mut}=1$, i.e., only one copy in the A clone was mutated. This leads to the simplified equation:

$$TVP(AF, \alpha, A_{total}) = \frac{AF[2\alpha + (1-\alpha)A_{total}]}{(1-\alpha)}$$

For each SSNV, the inventors calculated the allele frequency by dividing the number of variant reads by the number of total reads at the position. Standard 99% binomial CI was calculated for the estimate of allele frequency using the binom.test function in R. The formula for TVP above was then used to convert these into estimates and 99% confidence intervals for the TVP.

Figure 4:
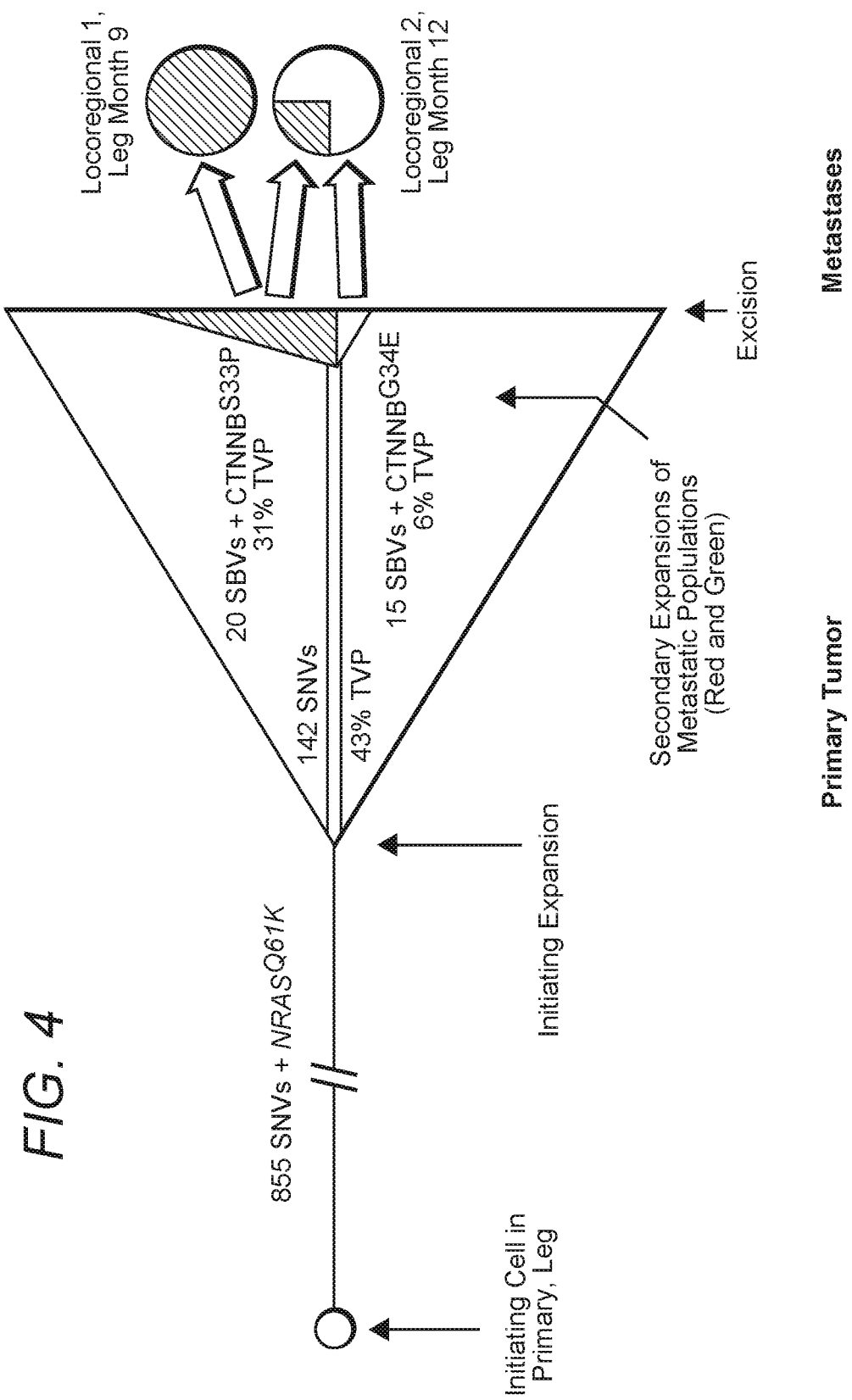
FIG. 4 schematically shows an integrated portrait of metastatic subclone formation, departure, and arrival for a selected patient.

Distinguishing groups of SSNVs defining tumor subclones: The large number of SSNVs in the study increases the risk of spurious false positives when identifying a tumor subclone based purely on a single SSNV. The inventors therefore searched for groups of SSNVs demonstrating concordant changes in TVP between samples, which would provide much greater support for existence of a distinct tumor subclone. To identify such concordant changes, only for regions of normal copy number, TVPs of all SSNVs from one tumor were mapped against their TVPs in each other tumor from that patient. The resulting graphs were visually examined for evidence of clusters of SSNVs distinct from shared clonal SSNVs (TVP of 1,1). Such a pattern was only detected in one patient (patient C). SSNVs from each sample of that patient were split into groups according to a threshold on their TVP value. The threshold was determined by Otsu's method (Otsu N (1979) A Threshold Selection Method from Gray-Level Histograms. IEEE Transactions on Systems, Man and Cybernetics 9(1):62-66), which utilizes a brute-force approach that tests every possible threshold that splits a set of values into two groups and then selects the threshold that minimizes the total intra-group variance. The thresholds selected for each sample, t_primary=0.55, t_locoregional1=0.29, and t_locoregional2=0.35, were integrated to define a set of SSNV groups for the tumors of the patient. A total of 6 groups were possible by choosing points above & below each threshold in a combinatorial manner, e.g., group 1 is the set of points>t_primary, >t_locoregional1, and >locoregional2, group 2 are the set of points<t_primary, >t_locoregional1, and <t_locoregional2, and so on until every combination of the three thresholds are made. Groups with fewer than 2 SSNVs were removed. The four remaining groups shown in FIG. 4 are described as follows: Group #1/yellow (>t_primary, >t_locoregional1, >t_locoregional2)=855 SSNVs; Group #2/blue (<t_primary, >t_locoregional1, >t_locoregional 2)=142 SSNVs; Group #3/red (<t_primary, >t_locoregional1, <t_locoregional 2)=20 SSNVs; Group #4/green (<t_primary, <t_locoregional1, >t_locoregional 2)=15 SSNVs.

Figures 1, 3A:
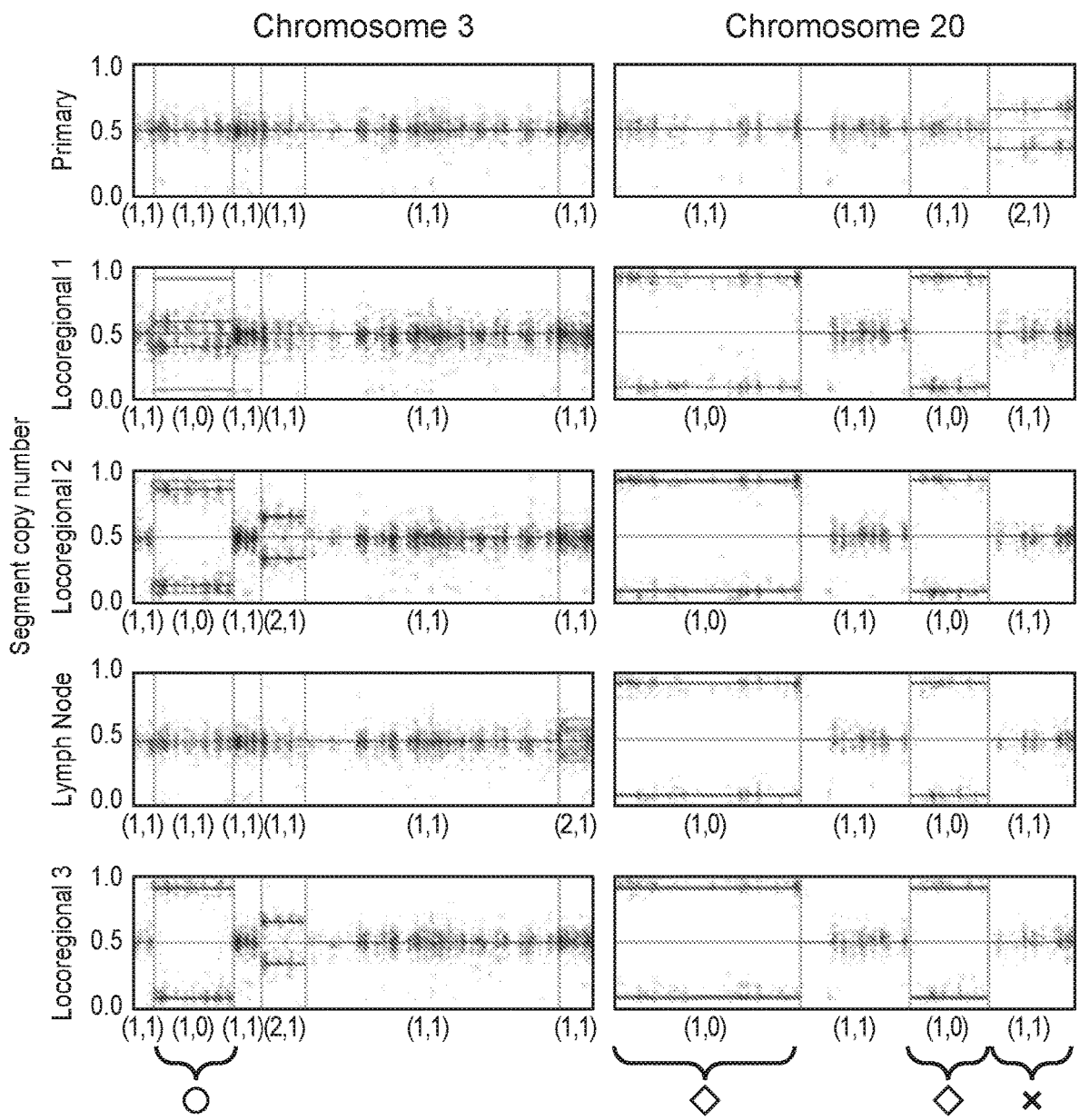
FIG. 3A shows exemplary scatter graphs for tumors of a selected patient, the allelic fraction of heterozygous SNPs along chromosomes 3, 20, and 14, and location of the primary tumor and metastases.
Figures 2, 3A:
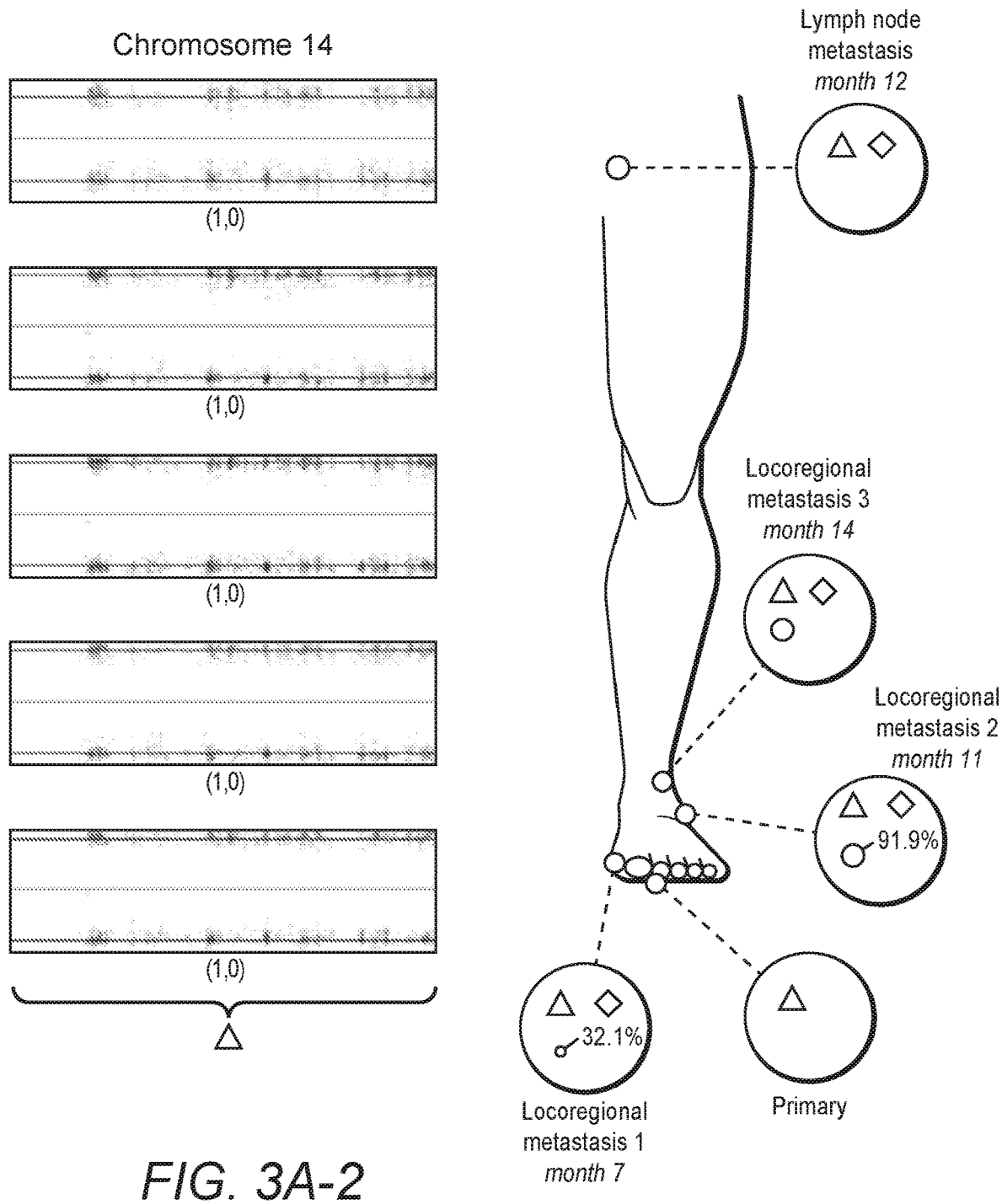
Figures 1, 3B:
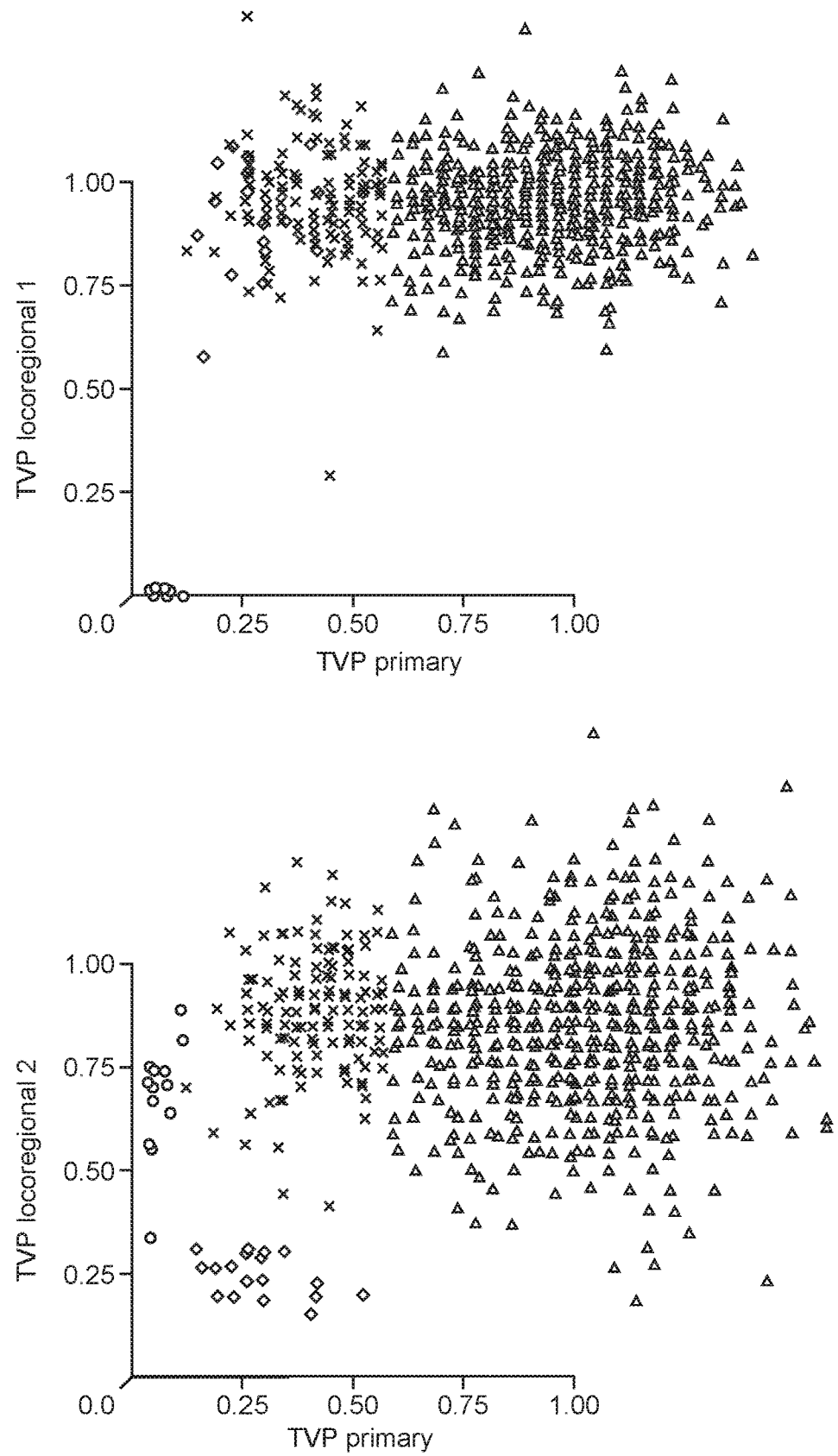
FIG. 3B shows exemplary plots correlating TVPs for all SSNVs between primary tumor and metastases, and location of the primary tumor and metastases.
Figures 2, 3B:
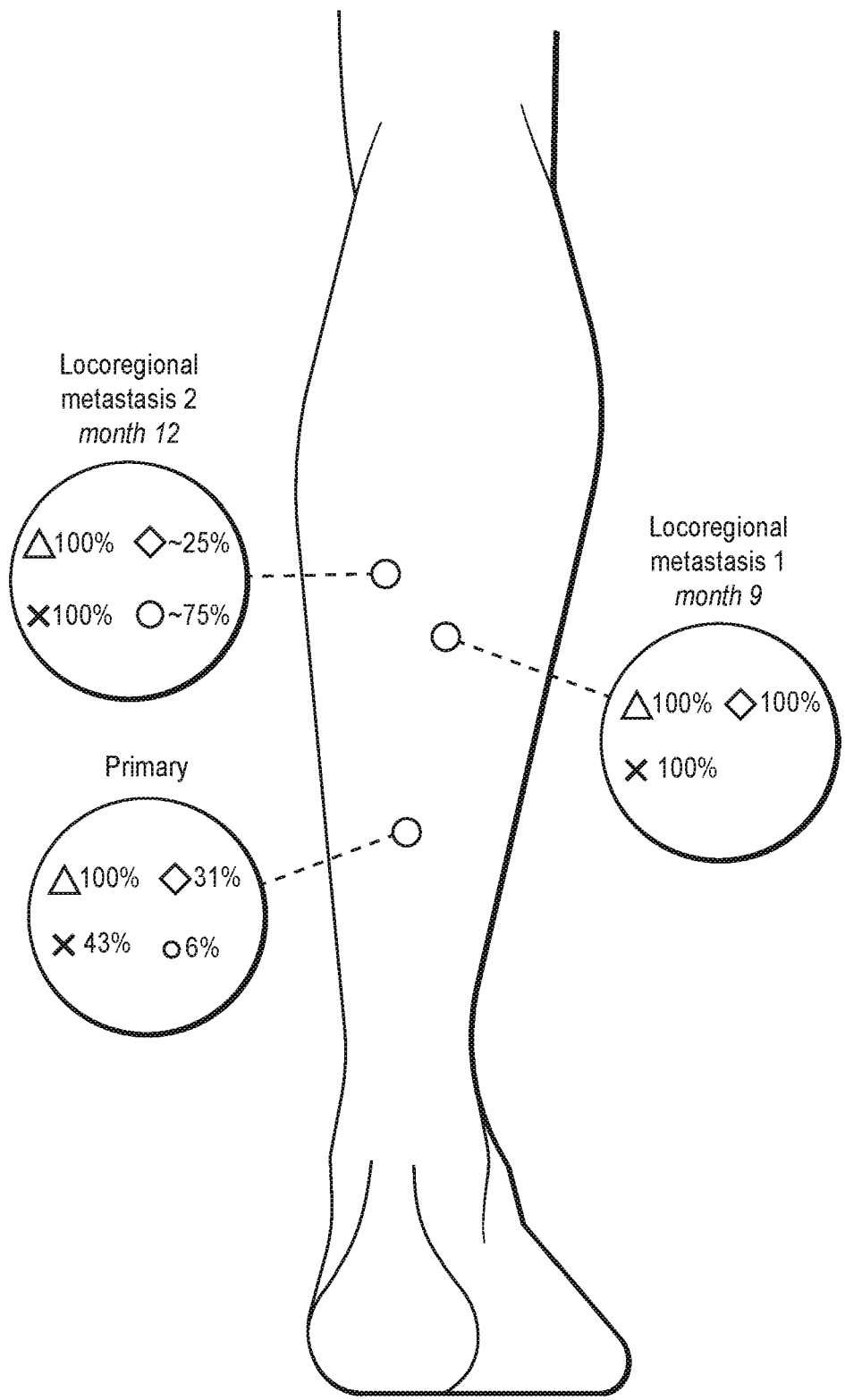

The TVPs for the SSNVs in Group #1 extend leftward in FIG. 3B, approaching 0.55. It is theoretically possible that some these Group #1 SSNVs with the lowest TVPs may actually be at subclonal abundance. However, if this were the case, they would still segregate identically with the blue Group #2 SSNVs, reaching fully clonal abundance in both locoregional metastasis 1 and 2, and thus would not alter the conclusions regarding the cell populations founding metastases.

Calculation of tumor variant percentage (TVP) and 99% confidence intervals for CNAs: The inventors used the bias-corrected estimates of the allele frequency of the majority allele (described in the previous paragraph) to compute TVP for each CNA region, representing the proportion of cells in the tumor containing the CNA. Given the normal cell contamination estimate, α, the percentage of tumor cells with the major allelic state A and minor allelic state B was calculated using the following equation:

$$TVP(AF, \alpha, A_{maj}, B_{maj}, A_{total}, B_{total}) =$$
$$\frac{(1-\alpha)B_{maj} + \alpha - AF[2\alpha + (1-\alpha)B_{total}]}{AF(1-\alpha)(A_{total} - B_{total}) - (1-\alpha)(A_{maj} - B_{maj})}$$

$A_{maj}$, $B_{maj}$, $A_{total}$, and $B_{total}$ are the majority allele copy number and the total copy number of the A and B allelic states, respectively, assuming the segment was diploid in the matched normal DNA. If the TVP value was greater than 1.0 or less than 0.0, it was truncated to be within this range. If the estimate of TVP was less than 0.5, the A and B allelic states were swapped so that the allelic state A remained the dominant clone.

The derivation of the equation for the TVP for a CNA region follows that described previously for a SSNV. The difference here is that the allele frequency is now the allele frequency of the majority allele strand, rather than the allele frequency of a mutation at a single nucleotide, and the number of copies of the majority allele ($A_{maj}$,$B_{maj}$) take the place of the number of copies that contain the mutation ($A_{Mut}$,$B_{Mut}$). Furthermore, since for CNAs one is interested in comparing populations A and B that have different copy number alterations, the inventors no longer made the simplifying assumptions regarding the values of $A_{maj}$, $B_{maj}$, $A_{total}$, and $B_{total}$ that were made in the analysis of SSNVs.

The estimate of TVP was determined by applying the above formula to the estimate of the AF of the majority allele, as determined by the allele frequencies in the SNPs contained in the region and corrected for bias as described in the next section. The confidence intervals for TVP were calculated by applying the formula to the upper and lower 99% bootstrap confidence intervals of the AF. If the confidence interval of the TVP was greater than 0.01 and less than 0.99, then the curated region was considered to be a mixture of two allelic states, and therefore deemed subclonal. Only CNAs for which such estimates and confidence intervals of the AF could be reliably calculated, as described in more detail below, were considered for estimation of TVP.

Correcting sources of bias in SNP allele frequency in the calculation of tumor variant percentage (TVP) for CNAs: In order to calculate the TVP of the CNAs, the inventors first estimate the allele frequency of the major allele, defined as the number of strands of DNA in all cells that come from the major allele. To do so, the individual SNPs in the region were used, each of which provides an independent estimate of the major allele frequency, and combined together to get a single estimate of allele frequency.

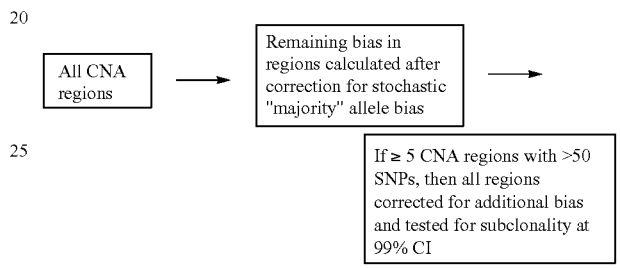

As described earlier, the average majority allele fraction is simply calculated for heterozygous SNP in the normal tissue as $$AF_i^t = \frac{DP_{i,maj}}{DP_{i,total}}$$

where $DP_{i,maj}$ is the read depths of the germline allele with the greatest read support and $DP_{i,total}$ is the total read depths at the position i in the tumor. If it were possible to comprehensively phase SNPs as in whole genome sequencing data, random variation in the allele frequency across SNPs would average to 0.5. However, as phasing is very limited in exome sequencing data, as in this study, the inventors relied on the read depths to phase the SNPs as well as estimate the allele frequency. This generates a small, persistent bias based on misidentification of a "majority" allele as the result of stochastic sampling error (i.e., those values slightly above 50%), with the bias being larger when the true allele frequency is closer to 0.5, namely regions where both alleles have equal copy number. The bias also depends on the sequencing depth, with SNPs with larger depth giving less biased estimates.

In identifying CNA regions and estimating their copy number, the inventors accounted for this bias in a way that did not require information about their copy number status and relied on using the observed AF for the SNP in the normal to correct for the bias. In calculating the AF for TVP calculation for CNA regions, the inventors assume that the copy number status has been correctly identified, and in this setting the inventors more formally calculated a SNP specific bias correction based on a probabilistic model.

It is assumed for a CNA that the dominant clone of the region was identified, and that this dominant clone has allele specific copy number C, for example C=(2,1). C implies an allele frequency for the major allele in the dominant clone, adjusted for normal contamination α, which was designated as p=p (C,α). Then the corrected estimate of allele frequency of an individual SNP is given as $$AF_{i,corr}^t = AF_i^t - f_{m_i}(p) - g(C),$$

$f_{m_i}(p)$ is the expected bias for the allele frequency p based on a binomial model and is specific to the sequencing depth of that SNP. g(C) is a further bias correction applied to all SNPs in the CNAs with the same dominant clone copy number C, and the determination of $f_{m_i}(p)$ and g(C) is described in more detail below.

The inventors calculated $AF_{i,corr}^t$ for all SNPs in the CNA region, restricting analysis to SNPs with sequencing depth m>50, and to those SNPs where the normal tissue had $AF_i^n \leq 0.7$. Furthermore g(p) was not able to be reliably estimated for some dominant clone values, as described more fully below. In order to estimate the allele frequency of the entire CNA region, the median of the n individual $AF_{i,corr}^t$ estimates were taken (where n is the number of SNPs in the CNA region).

The inventors calculated 99% confidence intervals of the allele frequency via a non-parametric bootstrap: resampling of the $AF_i^t$ (corr) values and calculating the median, then repeating 5,000 times. The 99% confidence intervals are the 0.025 and 0.975 quantiles of the bootstrap resampling distribution, truncated to be between 0 and 1 (inclusive).

Derivation of $f_{m_i}(p)$: For each SNP if one knows the true allele frequency p, one can calculate the expected bias of $AF_i^t$ under a binomial distribution, Bin(p, $m_i$); in what follows the subscript i is dropped for simplicity. Since the sequencing depth, m, is generally large, a normal approximation for the expected bias was used:

$$E(AF^t) - p = f_m(p) = (1-2p)\Phi(\alpha_p) + 2\sqrt{\frac{p(1-p)}{m}}\phi(\alpha_p)$$

where $$\alpha_p = (1/2 - p)\left(\frac{p(1-p)}{m}\right)^{-1/2}$$

and φ and Φ are the standard normal density and cumulative distribution (CDF) functions, respectively. For p>0.6, $f_m(p)$ is generally negligible. This gives an initial bias-corrected estimate of the allele-frequency $$AF_{corr}^t = AF^t - f_m(P)$$

where p is taken to be the allele frequency implied by the allele-specific copy number for the dominant clone in the CNA, adjusted for normal contamination α (so that p=0.5 for SNPs in (1,1) and (2,2) regions). Again, only for regions with $_p$=0.5 for the dominant clone will this bias correction be non-negligible. In such CNA regions, if the region is truly subclonal this estimate will generally be an over-estimate of the bias, making the detection of the subclonal region more conservative (since $AF_{corr}^t$ will be pulled closer to 0.5).

Derivation of g(C): A close inspection of the results using this approach indicated that some, but not all, bias was accounted for by this stochastic model (and therefore corrected by subtracting off $f_m(p)$). When expected bias $f_m(p)$ was compared to the observed values of $AF_i^t$ across the thousands of SNPs that come from regions with p=0.5, it was observed that $f_m(p)$ slightly underestimated the bias in the observed data. Moreover, this difference was different for different samples, and was also different from what was observed when comparing the normal SNPs ($AF_i^n$) to their expected bias. A similar difference was observed between the expected allele frequency and the observed allele frequency in regions with an expected majority allele frequency not equal to 0.5 (and therefore not affected by the bias in calculating the allele frequency). For some samples, there were a sufficient number of regions of a similar allelic copy number to observe that this was a shared bias, not due to subclonality. Since the estimate of subclonality rests on finding differences between the observed and expected allele frequency, this difference could result in falsely detecting subclonality.

There are several understood reasons why such systematic bias may persist. For example, by mapping to a reference genome, SNPs missing from databases or SSNVs will reduce successful mapping and favor an arbitrary allele. To reduce the impact of such other forms of systematic bias, the inventors further corrected the observed allele frequency of each SNP by calculating the median value of this difference across all SNPs with the same allelic copy number (e.g. (1,0)), denoted as g(C). The inventors subtracted g(C) from $f_m(p)$ before calculating the final bias-corrected estimate of allele frequency. The inventors only did this for tumor samples with sufficient numbers of regions to be able to do this robustly so that no region unduly influenced the adjustment of the expected value of the allele frequency. Specifically, for calculating g(C) the inventors only considered regions that had at least 50 SNPs with sequencing depth greater than 100 and further required the sample to have at least 5 such regions with the same allelic copy number. If a sample had fewer than 5 regions of a specific allelic copy number or if any single region contained greater than 30% of the total SNPs for a given allelic copy number, then regions with that allelic copy number did not have an estimate of g(C) and therefore were not given allele frequency estimates for the purposes of subclonality estimation. The total number of segmented regions per series ranged from 29 to 76 across the seven series. Those that satisfied the criteria and received an allele frequency and thus a TVP estimate ranged from 23 to 49 (60-96% of segments).

The number of somatic single nucleotide variants (SSNVs) detected varied from 96 to 115 per exome in primary melanomas from acral or intermittently exposed skin (patient E: heel, patient B: back) to more than 4,900 in primary melanomas from chronically sun-exposed sites, corresponding to 4,800 to 245,000 mutations per genome (7/8 patients with high-confidence copy number estimates for all tumors are shown in FIG. 1). SSNVs detected at any allele frequency (AF) in the primary melanomas and all corresponding metastatic tissues were considered fully shared (bottom black tier, FIG. 1), including known oncogenic mutations in melanoma such as BRAFV600E, CTNNB1S33P and in the TERT promoter. Fully shared variants detected at fully clonal AFs (i.e. ~100%) in the primary tumor were considered "ancestral"—they occurred early during population expansion of the cells comprising the primary tumor, before any metastases had formed. In contrast, SSNVs not fully shared between primary tumor and metastatic tumors revealed distinct evolutionary histories and are shown in the upper portion of FIG. 1 as partially shared (dark grey) and private (light grey).

Using DNA extracted from additional tissue sections of tumors of patients A, C, E, F, and G, the inventor validated with ion semiconductor sequencing at an average depth of 953 reads the AFs of 72 representative SSNVs originally discovered by exome sequencing. All SSNVs detected in metastases by exome sequencing were also detected by targeted sequencing. In several instances, SSNVs were only detected in some of multiple, independent tissue sections of the primary tumor, probably reflecting tumor heterogeneity of these variants.

There is controversy on whether melanoma sometimes disseminates widely without any regional interim stage. If metastatic dissemination cascaded from locoregional to distant locations, one would expect regional and distant metastases to reside on a common phylogenetic branch. SSNVs partially shared between the primary tumor and some, but not all metastases, revealed instances in which different subpopulations of the primary tumor seeded independent metastases in parallel rather than in series. In these cases, cells in the primary tumor both before and after acquisition of the partially shared variants must have established metastases. Exome sequencing in patients A, C, and F each clearly revealed two such distinct parental subpopulations in primaries shared only with some metastases. Therefore their metastases most likely arose from independent cells in the primary tumor, rather than evolving from other metastases.

In patient F, validation sequencing confirmed at least 2 SSNVs were present subclonally in the primary tumor, absent in the locoregional metastasis, yet detected in the lymph node and distant skin metastasis. Conversely, at least 2 SSNVs were present subclonally in the primary tumor, absent in the lymph node and distant metastases, yet present in the locoregional. Thus the inventor concluded that the locoregional tumor arose from a cell population in the primary distinct from the one generating the lymph node and distant metastasis.

In patient H, a deletion of one copy of chromosome 4 was seen in the primary tumor and the brain metastasis, yet absent in the lymph node and locoregional skin metastases, showing the latter tumors could not have given rise to the brain metastasis. Furthermore, the private mutations from both the lymph node and brain metastasis harbored a predominance of C>T substitutions (1725/1849 and 804/973 SSNVs respectively), suggesting that these metastases also arose from different cells in the primary tumor. It is unlikely that these UV-driven mutations were acquired in a tumor other than the primary tumor.

In patient D, where the primary tumor was found in the right leg, four SSNVs were partially shared by the groin lymph node and in transit right leg locoregional metastases, while five additional SSNVs were partially shared by only the two locoregional metastases. The anatomic relationship makes it unlikely that cells in the groin lymph node returned to found multiple locoregional metastases only in one foot, close to the primary tumor. Therefore the inventor contemplates that the five partially shared SSNVs were acquired in distinct cells of the primary tumor, some of which left to disseminate and form two distinct subpopulations in the locoregional metastases.

In patient E, a cell population harboring an interstitial deletion of the wild-type copy of CTNNB1 was detected at subclonal proportions in two separate metastases, strongly suggesting that they were founded by a single, undetected cell subpopulation in the primary tumor. Overall, 6 of 8 of the patients showed clear evidence of parallel dissemination of metastases from the primary tumor.

Figure 2:
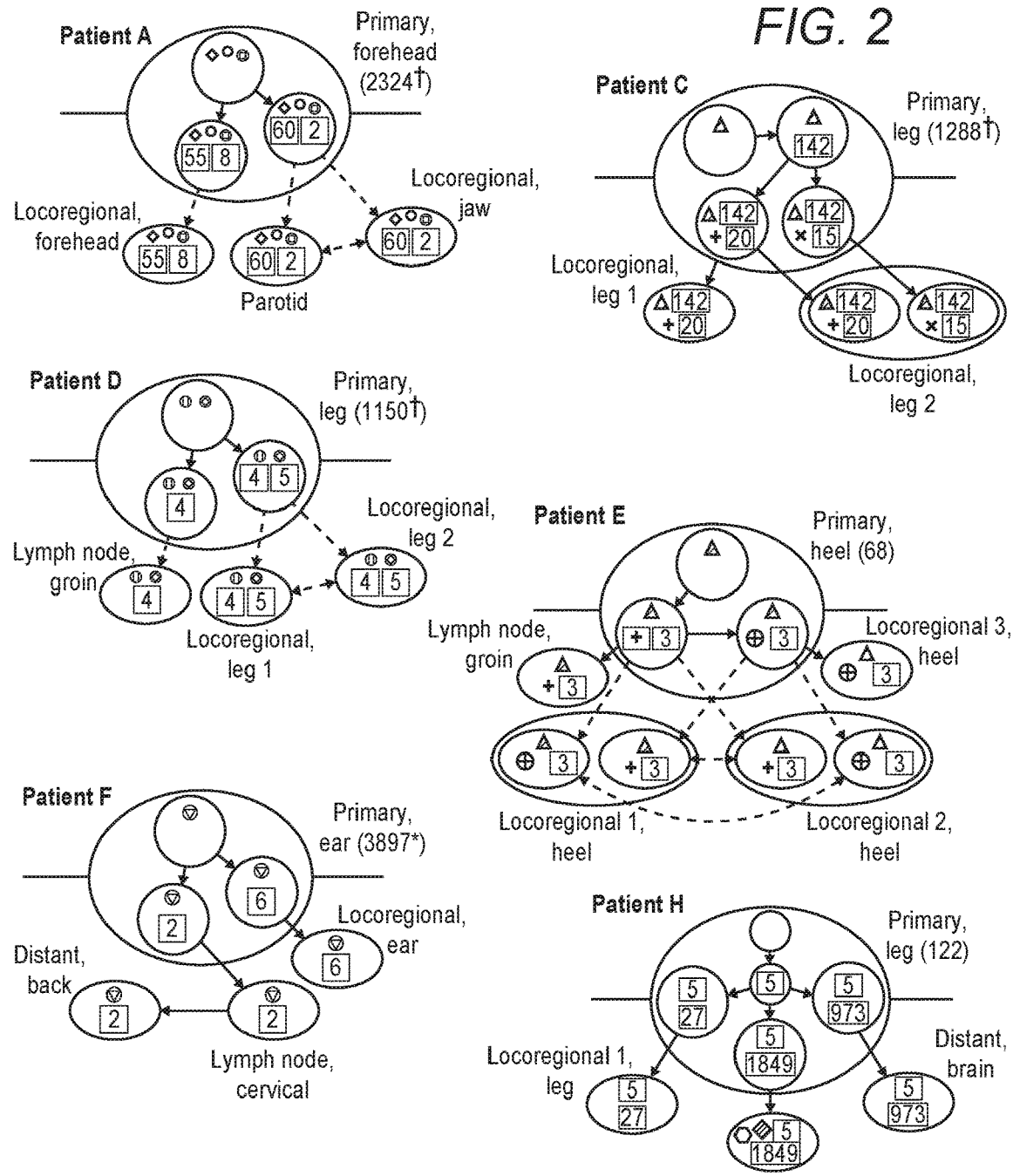
FIG. 2 schematically illustrates phylogenetic profiles of primary tumor and their metastases for selected patients based on the status of the SSNVs.

FIG. 2 exemplarily illustrates translation of the classification information into a phylogenetic map. As can be readily seen, metastases depart the primary melanoma in parallel, from genetically diverged cell subpopulations. For patients A, C, D, E, F, and H, phylogenetic history of the metastasizing cells is reconstructed based on sequencing of fresh and FFPE portions of each tumor. Solid arrows denote probable dissemination routes, while dotted arrows denote multiple possible paths. Numbers in squares denote partially shared SSNVs. Instances of SSNVs deduced to be in the primary tumor, but not detected directly by sequencing, are color-coded by line of reasoning. The patterns of dissemination demonstrate that metastases in each patient derived from distinct cells in the primary tumor, which often demonstrate extensive genetic divergence from each other.

Copy number aberrations (CNAs) with read counts from exome sequencing significantly below the expected threshold for full clonality were considered subclonal. Each patient had at least one tumor with such subclonal CNAs (range 1-10 per patient, with a maximum of 6 per tumor. Subclonal CNAs in the primary tumor must have arisen after the lesion was founded. Any metastasis founded from cells of such a subclones should harbor that new aberration in every cell.

Unexpectedly, in patient E, the identical 34 Mb interstitial deletions on chromosome 3 deleting CTNNB1 were observed in both locoregional metastases 1 and 2 at subclonal levels as is schematically illustrated in FIG. 3A. Given the identical flanking breakpoints shared by the deletions, it is unlikely that they arose independently in these two metastases. The inventor concluded therefore that these metastases must each have been founded by at least two cell populations: one harboring the deletion and one without. In no other patients was the inventor able to identify identical, unique, subclonal CNAs in more than one metastasis.

With further reference to FIG. 3A, the scatter graphs chart show on the y-axis, for tumors of patient E, the allelic fraction of heterozygous SNPs along chromosomes 3, 20, and 14. Shown are the primary tumor, three locoregional metastases, and a lymph node metastasis, ordered from top to bottom according to time of clinical presentation. Divergence of the allelic fractions from 0.5 indicate a copy number change. The resulting allelic states are shown in the red numbers underneath each segment. Grey lines depict the expected allelic fraction, if the CNA were present in all cells of the tumor, taking into account the normal cell contamination. Dark grey lines indicate the observed average copy number level for each CNA. The 33.9 Mb region on chromosome 3 represented by the circle shows a subclonal deletion in locoregional metastases 1 (TVP=32.1%, 99% CI=28.0-35.6%) and 2 (TVP=91.9%, 99% CI=90.4-93.2%) and fully clonal deletion in metastasis 3 (TVP=100%). Chromosome 20 shows two separate deletions reaching from 0-25.53 Mb and from 40.39-50.93 Mb, respectively, represented by the diamond, which are present at fully clonal levels in all metastases but absent in the primary tumor. One entire copy of chromosome 14 is deleted at fully clonal levels in all tumors and is thus considered fully shared (triangle). The presence of the deletion from 9.72-43.6 Mb of chromosome 3 at subclonal levels in locoregional metastases 1 and 2 suggests at least one of these tumors was founded by two distinct cell populations: one harboring the chromosome 3 deletion and one without.

The scatter graphs in FIG. 3B show, for patient C, the TVPs for all SSNVs in genomic regions not affected by copy number changes. Shown are the TVPs for the primary tumor on the x-axes and the locoregional metastases 1 (upper graph) and 2 (lower graph) on the respective y-axes. Fully shared SSNVs are depicted as triangles and are present in all tumors at fully clonal levels. A subclone present in approximately 30% of the cells of the primary tumor (x) is present at close to fully clonal levels (TVP=100%) in both metastases. A second subclone with TVP of 25% in the primary tumor (diamonds) is fully clonal in metastasis 1 but at a TVP of 25% in metastasis 2, suggesting that metastasis 2 was seeded by at least two genetically distinct founding cells, one containing the SSNVs depicted as red diamonds and one without. A third subclone present at 3% in the primary melanoma, (circle) is absent in metastasis 1 but present at ~75% abundance in metastasis 2, indicating that it has contributed partly, but not entirely, to the cells of metastasis 2. This third subclone therefore also indicates that metastasis 2 was founded by two genetically distinct populations.

It was then investigated if the SSNV data could also reveal multiple cell populations founding single metastases. Because individual SSNVs provide insufficient power to identify subclones definitively, the inventor searched for clusters of partially or fully shared SSNVs with similar subclonal AFs, indicative of subpopulations. The inventor estimated the percentage of tumor cells carrying each individual SSNV in diploid regions, taking into account the normal cell contamination and copy number at the locus harboring the SSNV. In only patient C, four such clusters of SSNVs were discerned, using a grouping algorithm, in the primary tumor and both metastases. Each of these four clusters of SSNVs showed coordinate changes in TVP between the primary tumor and two metastases.

The clusters generated by this algorithm make it clear that some fully clonal SSNVs in the primary tumor are also fully clonal in both metastases (triangles, FIG. 3B). Some subclonal SSNVs in the primary tumor are fully clonal in both metastases (x). Two other clusters of subclonal SSNVs present in the primary tumor at lower abundance (diamonds and circles) do not co-segregate in locoregional metastasis 1, indicating that each must reside in a different cell population. Surprisingly, however, both of these distinct subpopulations are detected in locoregional metastasis 2 in Patient C. Therefore, the sequencing data in both patients C and E suggest that their metastases were seeded not by single cells, but by at least two cells with distinct genetic identities.

Intriguingly, in both patients, the defining subclonal populations also included alterations in CTNNB1. In patient E, the interstitial deletion on chromosome 3 removed a wildtype copy of CTNNB1, leaving a hemizygous S33P mutation. In patient C, two different known oncogenic CTNNB1 variants were detected that appeared to have arisen in distinct tumor subpopulations, evidenced by their location within distinct clusters of SSNVs. The G34E variant, part of the SSNV cluster annotated with circles in FIG. 3B, was estimated to be present in 6% of the cells in the primary tumor, absent in locoregional metastasis 1, and present in 75% of cells in locoregional metastasis 2. By contrast, the S33P variant, in the SSNV cluster denoted by diamonds, was present in 31% of cells in the primary tumor, fully clonal in locoregional metastasis 1, and present in 25% of the cells of locoregional metastasis 2. Both subpopulations must have disseminated independently to locoregional metastasis 2. It is remarkable that known activating mutations in β-catenin emerged multiple times among these late-arising variants associated with metastases. Activation of the WNT signaling pathway (e.g. by β-catenin mutations) has also been implicating in promoting metastatic potential in mouse models of melanoma. The reconstructed evolution of metastatic dissemination in patient C is depicted in FIG. 4.

FIG. 4 exemplarily illustrates a situation where the ancestral cell harboring 855 SSNVs proliferated, generating the primary tumor. During expansion into the primary tumor, a specific cell acquired 142 more SSNVs and then two cells from that subpopulation subsequently acquired 15 more (light grey) and 20 more (dark grey) SSNVs. Intriguingly, each of these later-evolving subpopulations (light and dark grey, identical to those seen in metastases) each acquires a different known oncogenic CTNNB1 mutation. Both subclones are seen in locoregional metastasis 2, suggesting that once the ability to metastasize is acquired, the competent subclone can either reach existing metastases or travel with other metastatic subclones simultaneously.

As discussed above, in patients C and D, the inventor found evidence of stepwise evolution of the metastatic subpopulations in the primary melanoma, supporting a common progenitor of metastases that arose over time in the primaries. A distinct line of evidence supporting descent of metastatic cell populations from specific, subclonal populations in the primary tumor is the presence of SSNVs partially shared among all metastases but not detected in the primary tumor. In such cases, the population of cells in the primary tumor that spawned the metastases must either have: i) resided in the unsequenced portion or ii) resided at undetectable (<1%) subclonal levels in the sequenced portion or iii) originated from a separate metastasis not analyzed in this study. Three such SSNVs were detected in patient E and five such SSNVs were detected in patient H.

In Patient F, 4 SSNVs partially shared between the primary tumor and specific metastases were not detected in tissue representing at least 10% of the primary tumor used for exome and validation sequencing, indicating origin in a subclonal population in the remainder of the primary tumor. Therefore in 5 of 6 patients (C, D, E, F, and H) in whom metastases originated from at least two distinct subclonal populations in the primary tumor, these subclonal populations themselves descended from a common, parental subclonal population.

Thus, it should be noted that the present study presents several new insights into the process of metastatic dissemination. The collected material enabled the inventor to sample and analyze, at high sequence coverage, distinct regions of both primary melanomas and their matched metastases. The resulting data allowed the inventor to delineate and validate the phylogenetic relationship between tumor populations at different sites. This study provides evidence that metastatic dissemination can occur from different subpopulations of the primary tumor, which often disseminate in parallel rather than in serial fashion to form regional and distant metastases. The metastasis of genetically distinct cell populations from primary melanomas likely enhances the heterogeneity of tumor tissues, potentially contributing to drug resistance.

The sequential concept of metastatic dissemination is based on the clinical observation that regional metastases are often detected earlier than distant metastases. While explanations such as secretion of growth stimulating factors from the primary tumor have been proposed, the observation of multiple founding populations in metastases raises the possibility that regional metastases may grow faster because their proximity to the primary tumor increases the probability of repeated seeding events, as has been demonstrated experimentally in breast cancer.

It is conceivable that in some cases the multiple founding populations in metastases may be the result of disseminating cell clusters, as has been detected recently in both mouse models of melanoma and in patients. Interestingly, the circulating clusters in breast cancer also show enhanced signaling through catenin, a molecule also activated in several of the metastases. The phenomenon reported here in human melanoma patients may explain certain patterns of disease relapse of patients treated with targeted therapy. For example, if multiple metastases were partially founded by a specific cell population harboring a resistance variant, these metastases may simultaneously resume growth after an initial period of response. Such a pattern has been shown for MEK mutations in a patient whose BRAF mutant melanoma initially responded to RAF inhibition but then showed striking multifocal relapse.

Finally, the inventor demonstrated that the ability of cells to establish metastases can be a trait that emerges from a subclonal parent, suggesting changes are required in addition to the alterations required to establish the primary tumor. It is possible cells founding metastases repeatedly descended from a common parent simply by chance. However, in patients C and E, whose primaries harbored activating NRAS mutations, all six metastases were founded only by subclonal populations of the primary tumor that had acquired activated CTNNB1. Beta-catenin has previously been experimentally associated with metastasis in melanoma. Of the two cell populations metastasizing in patient C, each acquired a different, known activating mutation in beta-catenin (S33P and G34E), consistent with a necessity for CTNNB1 activation in forming metastases.

While later evolution of metastatic cell subpopulations has been reported in some pancreatic cancers, it was not detected in single-cell sequencing analysis of breast cancer metastasis. A model in which some primary melanomas require additional aberrations to metastasize may explain why their early detection and removal confers a survival benefit, as excision of tumors before the emergence of a clone with enhanced metastatic capability would be expected to be curative. If confirmed, these metastasis-enabling mutations could serve as biomarkers to identify primary melanomas at risk of dissemination.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of determining phylogeny of a metastasis and treating a melanoma patient, the method comprising:
    obtaining a plurality of respective nucleic acid sequences from a primary tumor, a first metastasis, a second metastasis, and non-tumor tissue collected from a melanoma patient;
    informationally coupling an analysis engine to a sequence database, wherein the sequence database stores the plurality of respective nucleic acid sequences;
    determining, by the analysis engine, somatic single nucleotide variants (SSNVs) for the primary tumor, the first metastasis, and the second metastasis relative to the nucleic acid sequences from non-tumor tissue of the patient by using an error probability model,
    wherein the error probability model comprises the steps of mapping short reads of the tumor sequences to the reference genome and determining error probability by using a statistical model that incorporates the mapping qualities, error probabilities from raw sequence quality scores, sampling of two haplotypes, and an empirical model for correlated errors at a site;
    filtering, by the analysis engine, the determined SSNVs;
    determining, by the analysis engine, a status for each SSNV with respect to each of the nucleic acid sequences from the primary tumor, the first metastasis, and the second metastasis;
    using, by the analysis engine, the status to classify each SSNV into a class selected form the group consisting of as a fully shared SSNV, a partially shared SSNV, a private SSNV, or an absent SSNV;
    using, by the analysis engine, the classifications of the SSNVs, to calculate a phylogenetic profile for the primary tumor, the first metastasis, and the second metastasis; and
    generating a targeted therapy for the melanoma, prepared for administration, wherein the targeted therapy recognizes or binds to the fully shared SSNV, wherein the fully shared SSNV is one that is present in the primary tumor, first metastasis and second metastasis.

2. The method of claim 1, wherein the step of determining SSNVs comprises a step of computing likelihoods of all possible genotypes for the primary tumor, the first metastasis, and the second metastasis.

3. The method of claim 1, wherein the step of determining SSNVs uses an error probability model.

4. The method of claim 1, further comprising a step of filtering the determined SSNV where the determined SSNV is heterozygous.

5. The method of claim 4, wherein the step of filtering comprises at least one of filtering by genotype quality, filtering by somatic score, filtering by mapping quality, filtering by quality sum of mismatches, filtering by average number of mismatches, filtering by fractional distance to 3'-end, and filtering by mutant allele depth.

6. The method of claim 1, wherein the status is 'present' or 'absent'.

7. The method of claim 1, wherein each class requires presence of at least three somatic single nucleotide variants, and wherein each of the somatic single nucleotide variants must have sufficient sequencing coverage to establish a tumor variant percentage with a 99% confidence interval of <1.

8. A method of determining phylogeny of a metastasis and treating a melanoma patient, the method comprising:
    obtaining a plurality of respective nucleic acid sequences from a primary tumor, a first metastasis, a second metastasis, and non-tumor tissue collected from a melanoma patient;
    informationally coupling an analysis engine to a sequence database, wherein the sequence database stores the plurality of nucleic acid sequences;
    determining, by the analysis engine somatic single nucleotide variants (SSNVs) for the primary tumor, the first metastasis, and the second metastasis relative to the nucleic acid sequences from non-tumor tissue of the patient, wherein the step includes a determination of likelihood for a possible genotype using an error probability model;
    wherein the error probability model comprises the steps of mapping short reads of the tumor sequences to the reference genome and determining error probability by using a statistical model that incorporates the mapping qualities, error probabilities from raw sequence quality scores, sampling of two haplotypes, and an empirical model for correlated errors at a site;
filtering, by the analysis engine, the determined SSNVs;
identifying, by the analysis engine, for each of the primary tumor, the first metastasis, and the second metastasis fully shared SSNVs, partially shared SSNVs, private SSNVs, and absent SSNVs;
calculating, by the analysis engine, a phylogenetic profile for the primary tumor, the first metastasis, and the second metastasis based on the fully shared SSNVs, partially shared SSNVs, private SSNVs, and absent SSNVs; and
generating a targeted therapy for the melanoma, prepared for administration, wherein the targeted therapy recognizes or binds to the fully shared SSNV, wherein the fully shared SSNV is one that is present in the primary tumor, first metastasis and second metastasis.

9. The method of claim 8, wherein the plurality of nucleic acid sequences are exome nucleic acid sequences or whole genome nucleic acid sequences.

10. The method of claim 8, wherein the plurality of nucleic acid sequences are in SAM or BAM format.

11. The method of claim 8, wherein the step of determining SSNVs comprises a step of computing likelihoods of all possible genotypes for the primary tumor, the first metastasis, and the second metastasis.

12. The method of claim 8, further comprising a step of filtering the determined SSNV where the determined SSNV is heterozygous.

13. The method of claim 12, wherein the step of filtering comprises at least one of filtering by genotype quality, filtering by somatic score, filtering by mapping quality, filtering by quality sum of mismatches, filtering by average number of mismatches, filtering by fractional distance to 3'-end, and filtering by mutant allele depth.

14. The method of claim 8, further comprising a step of determining allelic state for the SSNVs.

15. The method of claim 8, further comprising a step of determining a copy number aberration.

* * * * *